US008852587B2

(12) United States Patent
Korth et al.

(10) Patent No.: US 8,852,587 B2
(45) Date of Patent: Oct. 7, 2014

(54) ANTI-PRION PROTEIN ANTIBODY FRAGMENT

(75) Inventors: Carsten Korth, Dusseldorf (DE); Lothar Stitz, Kiebingen (DE); Benjamin Petsch, Tubingen (DE); Andreas Müller-Schiffmann, Odenthal (DE); Sirik Rutger Leliveld, Dusseldorf (DE)

(73) Assignees: Carsten Korth, Düseldorf (DE); Lothar Stitz, Kiebingen (DE); Benjamin Petsch, Tubingen (DE); Andreas Müller-Schiffmann, Odenthal (DE)

( * ) Notice: Subject to any disclaimer, the term of this patent is extended or adjusted under 35 U.S.C. 154(b) by 324 days.

(21) Appl. No.: 12/999,045

(22) PCT Filed: Jun. 16, 2009

(86) PCT No.: PCT/EP2009/004358
§ 371 (c)(1),
(2), (4) Date: Jan. 18, 2011

(87) PCT Pub. No.: WO2009/153029
PCT Pub. Date: Dec. 23, 2009

(65) Prior Publication Data
US 2011/0098448 A1 Apr. 28, 2011

(30) Foreign Application Priority Data

Jun. 17, 2008 (EP) .................................. 08010971

(51) Int. Cl.
*A61K 39/395* (2006.01)
(52) U.S. Cl.
USPC .................................................... 424/130.1
(58) Field of Classification Search
None
See application file for complete search history.

(56) References Cited

FOREIGN PATENT DOCUMENTS

| WO | 93/11155 A1 | 6/1993 |
| WO | 01/90191 A2 | 11/2001 |
| WO | 2004/050120 A2 | 6/2004 |

OTHER PUBLICATIONS

Donofrio, Gaetano et al.; "Paracrine Inhibition of Prion Propagation by Anti-PrP Single-Chain Fv Miniantibodies"; Journal of Virology; vol. 79, No. 13; Jul. 2005; pp. 8330-8338; XP002504979.
Perrier, Veronique et al.; "Anti-PrP antibodies block PrPSc replication in prion-infected cell cultures by accelerating PrPC degradion"; Journal of Neurochemistry; vol. 89, No. 2; Apr. 2004; pp. 454-463; XP002504981.
Peretz, D. et al.; "Antibodies inhibit prion propagation and clear cell cultures of prion infectivity"; Nature; vol. 412; Aug. 16, 2001; pp. 739-734; Nature Publishing Group, London, UK; XP002959453.
White, Anthondy R. et al.; "Monoclonal antibodies inhibit prion replication and delay the development of prion disease"; Nature; vol. 422, No. 6927; Mar. 6, 2003; pp. 80-83; Nature Publishing Group, London, UK; XP002275535.
Pankiewicz, J. et al. "P3-354 Monoclonal antibodies for the treatment of prion infection"; Neurobiology of Aging; vol. 25; Jul. 1, 2004; p. S456; Tarrytown, New York; XP004626117.
Sigurdsson, Einar M. et al.; "Anti-prion antibodies for prophylaxis following prion exposure in mice"; Neuroscience Letters; vol. 336, No. 3; Jan. 23, 2003; pp. 185-187; Limerick, Ireland; XP002275536.
Heppner, F.L. et al.; "Prevention of Scrapie Pathogenesis by Transgenic Expression of Anti-Prion Protein Antibodies"; Science; vol. 294; Jan. 2001; pp. 178-182; American Association for the Avancement of Science, US, Washington DC; XP001094132.
Pilon, John et al.; "Anti-prion activity generated by a novel vaccine formulation"; Neuroscience Letters; vol. 429, No. 2-3; Dec. 18, 2007; pp. 161-164; XP022364761.
Miyamoto et al.; "Inhibition of prion propagation in scrapie-infected mouse neuroblastoma cell lines using mouse monoclonal antibodies against prion protein"; Biochemical and Biophysical Research Communications; vol. 335, No. 1; Sep. 16, 2005; pp. 197-204; Academic Press, Inc., Orlando, Florida; XP005012155.
Mueller-Schiffmann, A. et al.; "Complementarity determining regions of an anti-prion protein scFv fragment orchestrate conformation specificity and antiprion activity"; Molecular Immunology (online); Retrieved from Internet on Nov. 20, 2008: URL:http://www.sciencedirect.com/science/article/B6T9R-4TT7OYF-1121 e0893ddc371a4a0b78fa8clec3bab81a; XP002504982.

*Primary Examiner* — Michelle S Horning
(74) *Attorney, Agent, or Firm* — Rankin, Hill & Clark LLP

(57) ABSTRACT

The invention relates to an antibody, antibody fragment or derivative thereof which specifically recognizes a prion protein and which comprises a complementarity determining region (CDR), a retro-inverso D-peptide of said CDR and/or an anti-idiotypic antibody, antibody fragment or derivative thereof which recognizes said CDR. The invention further concerns a nucleic acid molecule encoding said antibody, antibody fragment or derivative thereof as well as a method for generating an antibody, antibody fragment or derivative thereof that specifically recognizes a prion protein, wherein an antibody that recognizes a specific domain of the prion protein is generated, an antigen-specific amino acid sequence is isolated from said antibody, and an anti-idiotypic antibody, antibody fragment or derivative thereof, which recognizes said antigen-specific amino acid sequence, is generated.

9 Claims, 7 Drawing Sheets

Figure 1:
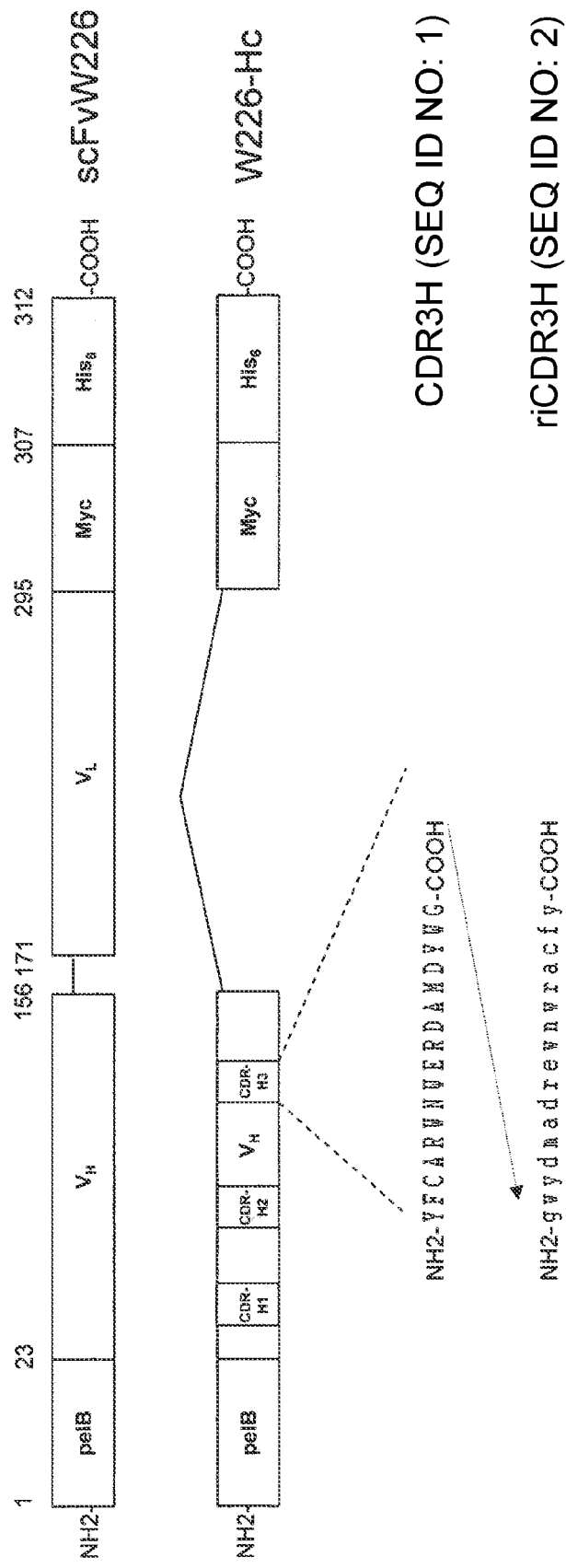

Fig. 6
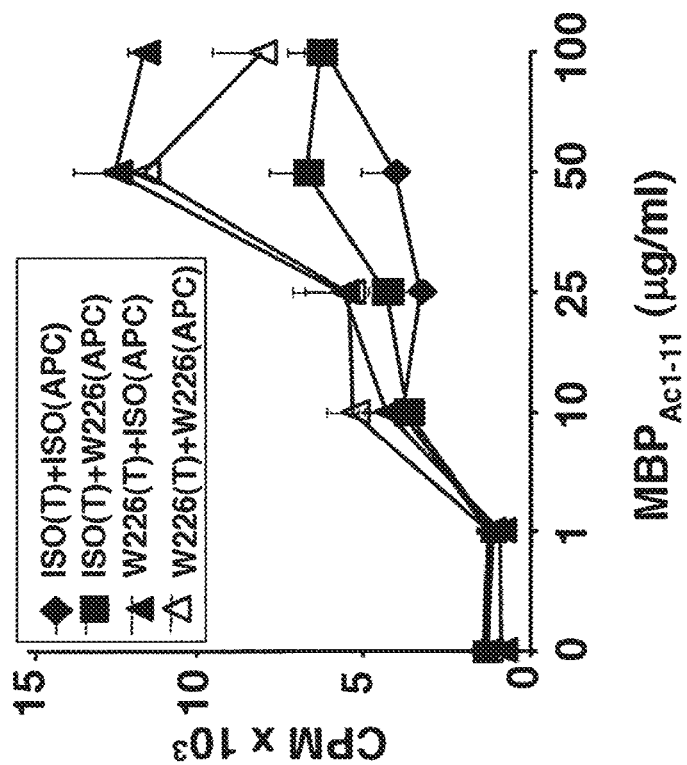
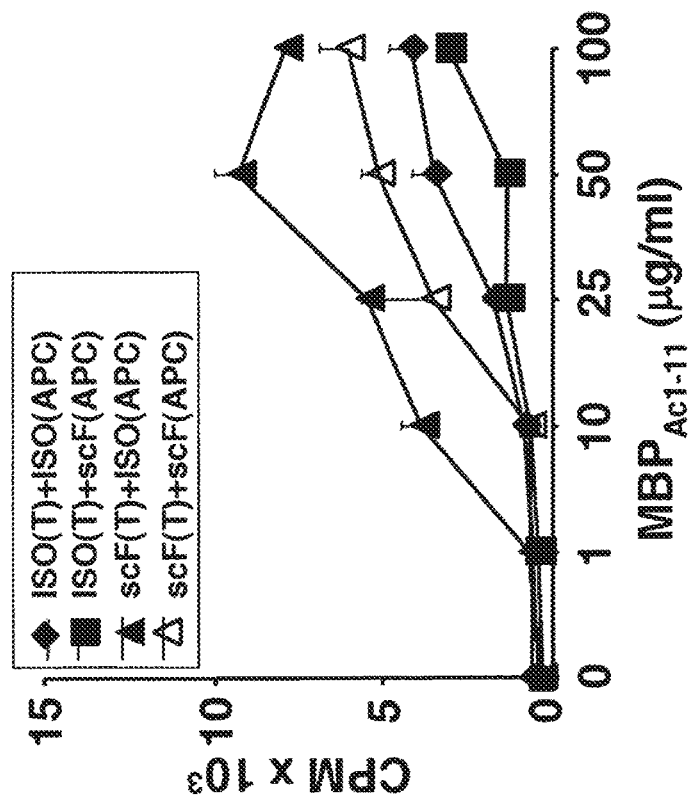

US 8,852,587 B2

ANTI-PRION PROTEIN ANTIBODY FRAGMENT

FIELD OF THE INVENTION

The invention relates to an antibody or antibody fragment which recognizes a prion protein. The invention further relates to a nucleic acid molecule encoding the antibody or antibody fragment and a method for generating the antibody or antibody fragment.

BACKGROUND OF THE INVENTION

Prion diseases are unique, transmissible, neurodegenerative diseases since the infectious agent consists solely of an alternative conformational isoform of the host-encoded prion protein, $PrP^{Sc}$, that replicates without a nucleic acid (Prusiner, 1982; Prusiner, 1998; Safar et al., 2005). Replication is thought to occur by induction of the infectious conformation in the normal prion protein $PrP^C$ (Prusiner, 1982). The different stable conformations, or "conformers", of PrP have pioneered the concept of protein conformational diseases within the neurodegenerative diseases stating that a misfolded or misprocessed protein is causative in the pathogenesis of the disease (Prusiner, 2001; Taylor et al., 2002). While due to the insolubility of many of the misfolded proteins, structural analysis has been difficult, generation of ligands specific for the misfolded proteins has been key to analyze these protein conformations in their cellular environment (Leliveld and Korth, 2007). The notion that soluble alternatively folded conformers or oligomers of proteins rather than insoluble protein deposits are instrumental in the disease processes has focussed efforts to develop conformer- or oligomer-specific ligands. Conformation-specific monoclonal antibodies (mABs) have been raised to $PrP^{Sc}$ (Korth et al., 1997; Paramithiotis et al., 2003) or to Aβ oligomers which are major pathogenic conformers in Alzheimer disease (Kayed et al., 2003), enabling detection of single conformers of proteins within a population of proteins. These reagents have become key reagents in detecting presence of these disease-associated conformers in tissues or body fluids as a method of identifying asymptomatic or early stage individuals at risk to developing prion disease (Kuhn et al., 2005; Nazor et al., 2005) or Aβ-oligomer related disease conditions (Lesne et al., 2006; Luibl et al., 2006).

So far, there is no pharmacotherapy of neurodegenerative diseases aimed at intervening with the fundamental biological causes of these diseases. Active or passive immunizaton approaches targeting disease-associated Aβ conformers in the case of Alzheimer disease (Schenk et al., 1999) or shielding the "normal" substrate conformer $PrP^C$ in the case of prion diseases (White et al., 2003) have been performed in mouse models of these diseases. Specifically, administration of mABs in preventing disease-associated symptoms in mouse models both of prion disease and Alzheimer disease (Bard et al., 2000; White et al., 2003). While in the case of anti Aβ mABs, these seem to pass the blood brain barrier (BBB) to prevent Aβ aggregation (Bard et al., 2000), anti-PrP antibodies for preventing prion disease has only been successful after peripheral (intraperitoneal) inoculation when they could act on peripheral sites of replication (Heppner et al., 2001; White et al., 2003). Thus, while anti-Aβ mABs seem to easily pass the BBB, anti-PrP mABs don't.

SUMMARY OF THE INVENTION

It is therefore one objective of the invention to provide an antibody or an antibody-like molecule that has improved BBB permeability and therapeutic options with antibodies for prion diseases.

According to the invention an antibody or antibody fragment is provided which specifically recognizes a prion protein, i.e. $PrP^C$ and/or $PrP^{Sc}$, and which comprises a complementarity determining region (CDR) according to SEQ ID NO:1, SEQ ID NO:11, SEQ ID NO:12 and/or SEQ ID NO:13, a retro-inverso D-peptide of said CDR according to SEQ ID NO:2, and/or an anti-idiotypic antibody or antibody fragment, which recognizes said CDR, comprising SEQ ID NO:3. An antibody or antibody fragment according to the invention that comprises the complementarity determining region 3 of the heavy chain (CDR3H) alone binds $PrP^{Sc}$ in a conformation-specific manner. An antibody or antibody fragment according to the invention that comprises an M13A or D11R mutant of CDR3H alone binds $PrP^{Sc}$ in a conformation-specific manner. An antibody or antibody fragment according to the invention that comprises an R10A mutant CDR3H alone binds $PrP^C$ in a conformation-specific manner. An antibody or antibody fragment according to the invention that comprises a retro-inverso D-peptide of CDR3H ((D-)CDR3H) binds specifically to $PrP^{Sc}$ and exhibits antiprion activity, demonstrating that these 16 amino acid-containing peptides, too, have potential as diagnostic and therapeutic agents in prion diseases.

An antibody or antibody fragment according to the invention that comprises an anti-idiotypic antibody or antibody fragment also exhibits antiprion activity, is able to immunoprecipitate specifically $PrP^{Sc}$ and can be used as an immunogen to circumvent self tolerance to this antigen. All antibodies or antibody fragments according to the invention bind either $PrP^C$ and/or $PrP^{Sc}$, have improved BBB permeability and offer new analytic and therapeutic options for prion diseases.

The term "antibody or antibody fragment", as used herein, comprises full length antibodies, fragments of antibodies such as $F_{ab}$ fragments or scFv, and single regions of antibodies such as complementarity determining regions (CDRs). However, this term may also comprise derivatives of said molecules, for example, retro-inverso peptides of antibody fragments or single CDRs.

In a preferred embodiment of the invention, the complementarity determining region (CDR) may be contained in at least one heavy chain variable region according to SEQ ID NO:4. The antibody or antibody fragment may further comprise at least one light chain variable region according to SEQ ID NO:5. In this case, it is advantageous if at least one heavy chain variable region and at least one light chain variable region are linked by a linker peptide, preferably $(Gly_4Ser)_3$. Thus, according to a preferred embodiment of the invention the antibody fragment is a scFv fragment comprising at least one heavy chain variable region according to SEQ ID NO:4 and at least one light chain variable region according to SEQ ID NO:5. The scFv fragment according to the invention binds specifically to $PrP^C$ and $PrP^{Sc}$ and exhibits antiprion activity so that it can be used in analysis and therapy of prion-related diseases.

In order to enhance excretion of a recombinant antibody or antibody fragment according to the invention, the antibody or antibody fragment may further comprise at least one signal sequence, preferably E. coli pelB or a similar leader peptide. Suitable targeting sequences are also, for example, tissue-specific or cell-specific antibody fragments that are capable of leading the antibody or antibody fragment according to the invention to desired target cells, in particular in brain. Further, signal peptides such as nuclear localization sequences (NLS) may be fused to the antibody or antibody fragment according to the invention in order to guide it within a target cell, for example into the nucleus. If an antibody or antibody fragment according to the invention further comprises at least one tag sequence, detection and/or purification of the antibody or antibody fragment can be facilitated. The tag sequence may be a c-Myc tag and/or an polyhistidine tag, preferably hexahistidine. Other tag sequences may be, for example, horse radish peroxidase, luciferase, or enhanced green fluorescent protein. That is, the antibody or antibody fragment according to the invention may be cloned and expressed as a fusion peptide or protein.

In a preferred embodiment of the invention, the antibody or antibody fragment according to the invention comprises the amino acid sequence according to SEQ ID NO:6, which is a scFv fragment comprising at least one heavy chain variable region according to SEQ ID NO:4 and at least one light chain variable region according to SEQ ID NO:5.

The invention includes antibodies or antibody fragments which, on an amino acid level, are at least 85%, preferably 90%, more preferred 95%, identical to the antibody or antibody fragment described above. Basically, the invention comprises all L- or D-peptide derivatives that can compete CDR3H or riCDR3H out of their interaction with PrPSc, and all L- or D-peptides where equivalently charged, hydrophobic, aromatic or hydroxyl amino acids are replaced within each other (positively charged equivalent amino acids: lysine and arginine, negatively charged equivalent amino acids: aspartate, glutamate; hydrophobic equivalent amino acids: alanine, valine, leucine, isoleucine, methionine; alcoholic equivalent amino acids: serine and threonine; neutral equivalent amino acids: glycine and proline).

The invention further includes a nucleic acid molecule selected from a group consisting of
  a) nucleic acid molecules encoding an antibody or antibody fragment comprising the amino acid sequence according to SEQ ID NO:1;
  b) nucleic acid molecules encoding an antibody or antibody fragment comprising the amino acid sequence according to SEQ ID NO:2;
  c) nucleic acid molecules encoding an antibody or antibody fragment comprising the amino acid sequence according to SEQ ID NO:3;
  d) nucleic acid molecules encoding an antibody or antibody fragment comprising the amino acid sequence according to SEQ ID NO:4;
  e) nucleic acid molecules encoding an antibody or antibody fragment comprising the amino acid sequence according to SEQ ID NO:5;
  f) nucleic acid molecules encoding an antibody or antibody fragment comprising the amino acid sequence according to SEQ ID NO:6;
  g) nucleic acid molecules encoding an antibody or antibody fragment comprising the amino acid sequence according to SEQ ID NO:11;
  h) nucleic acid molecules encoding an antibody or antibody fragment comprising the amino acid sequence according to SEQ ID NO:12;
  i) nucleic acid molecules encoding an antibody or antibody fragment comprising the amino acid sequence according to SEQ ID NO:13;
  j) nucleic acid molecules encoding the antibody or antibody fragment according to the invention;
  k) nucleic acid molecules comprising the nucleotide sequence according to SEQ ID NO:7;
  l) nucleic acid molecules comprising the nucleotide sequence according to SEQ ID NO:8;
  m) nucleic acid molecules comprising the nucleotide sequence according to SEQ ID NO:9;
  n) nucleic acid molecules comprising the nucleotide sequence according to SEQ ID NO:10;
  o) nucleic acid molecules, the polynucleotide sequence of which is at least 85%, preferably 90%, more preferred 95%, identical to the nucleotide sequence of a nucleic acid molecule of any of a) to n), and which encode an antibody or antibody fragment that specifically recognizes a prion protein;
  p) nucleic acid molecules, the complementary strand of which hybridizes to a nucleic acid molecule of any of a) to n), and which encode an antibody or antibody fragment that specifically recognizes a prion protein;
  q) nucleic acid molecules, the nucleotide sequence of which differs from the nucleotide sequence of a nucleic acid molecule of any of a) to p) due to the degeneracy of the genetic code; and
  r) nucleic acid molecules, the nucleotide sequence of which is complementary to the nucleotide sequence of a nucleic acid molecule of any of a) to q).

According to another aspect of the invention, a method for generating an antibody or antibody fragment that specifically recognizes a prion protein is provided. The method according to the invention comprises:

a) generating an antibody that recognizes a specific domain of the prion protein;

b) isolating an antigen-specific amino acid sequence from said antibody; and c) generating an anti-idiotypic antibody or antibody fragment, which recognizes said antigen-specific amino acid sequence.

This novel method of generating anti-PrP mABs overcomes the state of prior art and the previous notion that an effective immune response against PrP was impossible in wild type animals due to self tolerance. The present invention comprises therefore immunization with an antibody or antibody fragment binding to an interaction domain of PrP, which enables a prion protein to interact with another prion protein, and using it as an immunogen to circumvent self tolerance to this antigen. Surprisingly, if the specific domain is an interaction domain of the prion protein, the anti-idiotypic antibody recognizes $PrP^C$ and/or $PrP^{Sc}$ and has antiprion activity. In a preferred embodiment of the method according to the invention, the antigen-specific amino acid sequence is a complementarity determining region (CDR), preferably CDR3H according to SEQ ID NO:1 or a D-peptide retro-inverso sequence of CDR3H, termed riCDR3H, according to SEQ ID NO:2.

The invention further relates to a kit comprising the antibody or antibody fragment according to the invention and/or the nucleic acid molecule according to the invention.

The invention also concerns a pharmaceutical preparation comprising the antibody or antibody fragment according to the invention and/or the nucleic acid molecule according to the invention.

The antibody or antibody fragment according to the invention or the kit according to the invention or the pharmaceutical preparation according to the invention can be advantageously used in diagnosis and/or therapy of prion related diseases or other diseases where it has been demonstrated that manipulation of the prion protein by antibody/ligand binding influences the course of disease. The antibody or antibody fragment according to the invention or the kit according to the invention or the pharmaceutical preparation according to the invention can further be advantageously used for the purpose of eliciting an immunostimulatory effect.

DETAILED DESCRIPTION OF VARIOUS AND PREFERRED EMBODIMENTS OF THE INVENTION

According to the invention, a high-affinity, antiprion active scFv that could be expressed in high yields as a soluble protein targeted to the periplasmic space in *E. coli* is provided. Due to its reliable antiprion activity, the antibody fragment can be used for treating prion infections in vivo. The approximately 30 kDa protein is the smallest polypeptide fragment whose antiprion activity has ever been confirmed by bioassays, next to antiprion active Fab fragments that are about twice that big (Peretz et al., 2001). The antibody fragments according to the invention can be easily modified by recombination, if necessary, for shuttling the PrP-binding fragment across the BBB, and targeting it to the subcellular sites of action in the CNS and peripheral sites of replication.

Various exemplary and preferred embodiments of the invention are described below in detail with reference to the drawings.

BRIEF DESCRIPTION OF THE DRAWINGS

FIG. 1 shows a schematic drawing of one embodiment of the antibody fragments according to the invention. The variable heavy and light chain domains of W226, connected by a flexible $(Gly_4Ser)_3$-linker domain, (scFv) and W226-Hc were cloned into the procaryotic expression vector pET22b, allowing the secretion of the antibody fragments into the periplasm by an N-terminal pEL-B-leader sequence. In addition C-terminal myc- and $his_6$-tags were included. The sequence of the heavy chain CDR3 in L-(CDR3H) or retro inverso-form (riCDR3H) is shown beneath.

FIG. 2 shows a) A Coomassie-stained gel of the purification process involving metal affinity chromatography (IMAC) and subsequently PrP affinity chromatography (samples after single purification steps as indicated). The final fraction after elution from the PrP affinity column is pure (arrow).

b) An asymmetric flow field-flow analysis of scFvW226. Purified scFvW226 consisted of approximately 82% (w/w) monomers and 16% dimers. The largest particles that have been detected were probably tetramers (~120 kDa, ≤2%).

c. Quantitation of scFvW226-PrP binding by surface plasmon resonance spectroscopy (SPR). Recombinant mouse PrP was immobilized on a CM5-chip. ScFvW226 was injected at concentrations ranging from x to y at a flow rate of 30 µl/min. Association and dissociation curves were recorded for 180 s. After each analysis surface was regenerated with 10 mM NaOH. Curve fitting calculations yielded a $K_D$ of 2 nM.

d. A western blot of an immunoprecipitation of normal (N) and scrapie-infected (Sc) mouse brain homogenates with immobilized scFvW226. Starting material is blotted on the left panel. Normal homogenate is pulled down, and the pulled-down material form scrapie brains is protease-resistant indicating that scFvW226 recognizes both $PrP^C$ and $PrP^{Sc}$.

FIG. 3 shows a) A western blot of ScN2a cell lysates treated either by transfection with recombinant IgGκ-scFvW226 or by transfer with supernatant from non-infected, IgGκ-scFvW226-transfected N2a cell conditioned medium. ScN2a cells were either (from left to right) untreated, transfected with empty vector (pCDNA 3.1.), transfected with control IgGκ-scFv19B10, or IgGκ-scFvW226 for 4 days or 7 days. In addition, conditioned medium of N2a cells transfected with with control IgGκ-scFv19B10, or IgGκ-scFvW226 was used on ScN2a cells for 4 days. Furthermore, recombinant control scFv19B10 or scFvW226 generated in *E. coli* was used at a concentration of 10 nM for 7 days. The blot clearly demonstrates that all scFvW226-containing constructs are antiprion active.

b) A Western blot of ScN2a cell lysates treated with recombinant scFvW226 from *E. coli*. ScN2a cells were treated with different concentrations of scFvW226 as indicated, for one week. Subsequently, treatment was discontinued for either one week (upper panel) or three weeks ("set-off experiment"; lower panel). As controls, quinacrine (1000 nM) and full length mAB W226 (16 nM) were used. The blot demonstrates a permanent, dose-dependent, prion-clearing effect of recombinant scFvW226 in *E. coli*.

c) A western blot of ScN2a cell lysates treated with recombinant scFvW226 from *E. coli* to determine the minimal prion-clearing concentration. ScN2a cells were treated with different concentrations of scFvW226 as indicated for one week. At a minimal concentration of 4 nM, scFvW226 cleared prions.

FIG. 4 shows differential conformation-specificity and antiprion activity of single complementarity determining region 3 of the heavy chain (CDR3H) domain as an L-peptide and as a retro-inverso D-peptide ((D-)riCDR3H).

a) A western blot of PK-digested ScN2a cell lysates untreated (n. t.), treated with 1 µM quinacrine (Q), with recombinant heavy chain domain (W226-Hc) from *E. coli*, synthetic (D-)riCDR3H, or L-CDR3H at the concentrations indicated. Only (D-)riCDR3H had antiprion activity at 4 µM concentration.

b) A model of the surface representation of the linearized CDR3H peptides with the L-peptide at the top and the D-peptide below. Residues shown in blue and red are basic and acidic, respectively. It can clearly seen that the positions of the side-chain functionalities are conserved despite reversal of the amino acid sequence. Colors for atom positions are light red=O, light blue=N, gray=C, white=H, yellow=S.

c) A western blot of pulldown experiments from normal (N) or scrapie-infected (Sc) mouse brain homogenates with immobilized L-CDR3H or (D-)riCDR3H. Protease (PK) digestion at 200 µg/mL indicated the presence of $PrP^{Sc}$. Whereas scFvW226 could precipitate both $PrP^C$ and $PrP^{Sc}$ (FIG. 2*c*), the CDR3H region pulled down only $PrP^{Sc}$ in a conformation-specific manner, as did the (D-)riCDR3H peptide.

FIG. 5 shows staining of ScN2a cells with tetramethylrhodamine (TAMRA)-labeled L-CDR3H and (D-)riCDR3H. ScN2a cells were incubated with 1 µM (D-)riCDR3H-TAMRA (a) or L-CDR3H-TAMRA (d) for three hours and after washing with PBS, bound peptides were detected by fluorescence microscopy. To demonstrate the specificity of binding, ScN2a cells were preincubated with 100 µM scFvW226 30 min before addition of peptides (b and e). Digestion with trypsin demonstrated protease resistance of (D-)riCDR3H (c) vs. L-CDR3H (f).

FIG. 6 shows irradiated splenocytes from B10PL mice that served as antigen presenting cells (APC), and/or $MBP_{Ac1-11}$ T cell receptor (TCR) transgenic (Tg) $CD4^+$ T cells were treated with scFvW226 or mAB W226 and antigen (Ag). T cell proliferation was measured by $^3$[H] thymidine incorporation. APC and/or Ag-specific T cells were treated with (A) a single chain Fv fragment of W226 (scFv), or full length mAB W226 (B), or isotype controls (ISO). Targeting $PrP^c$ with any of these molecules resulted in the augmented proliferation of Ag-specific T cells.

FIG. 7 shows a Western blot of an immunoprecipitation experiment where a relative specificity for W226 to sheep prions, but not mouse prions can be seen. The two leftmost lanes depict the input sheep homogenate material (N=normal; Sc=scrapie) used for immunopreciptiation, then (from left to right) a control without antibody, and increasing concentrations of antibody (AB) as depicted. The two rightmost lanes are from mouse as a comparison. It can be seen that only high concentrations of W226 during the immunoprecipitation result in weak binding of PrP$^C$ from normal sheep homogenate whereas it pulls down readily PrP$^C$ from mouse brain homogenates.

EXAMPLES scFvW226 Construction, Expression, and Characterization

The original mAB W226 was derived from a hybridoma cell line generated after immunization with purified mouse PrP$^{Sc}$ For the IgG1 subtype mAB, a monovalent dissociation constant ($K_D$) with recombinant PrP was determined to be 0.5 nM (by surface plasmon resonance [SPR]) and, by immunoprecipitation, binding to both PrP$^C$ and PrP$^{Sc}$ was detected.

The variable light and heavy chains were cloned as a scFv into the pelB containing pET22b vector, including a (Gly$_4$Ser)$_3$-spacer (Huston et al., 1988) between H and L chain, and a C-terminal cmyc and His6 tag (see FIG. 1). The pelB leader sequence would target the protein to the bacteria's periplasmic space and generate a correctly folded and soluble protein.

Figure 2:
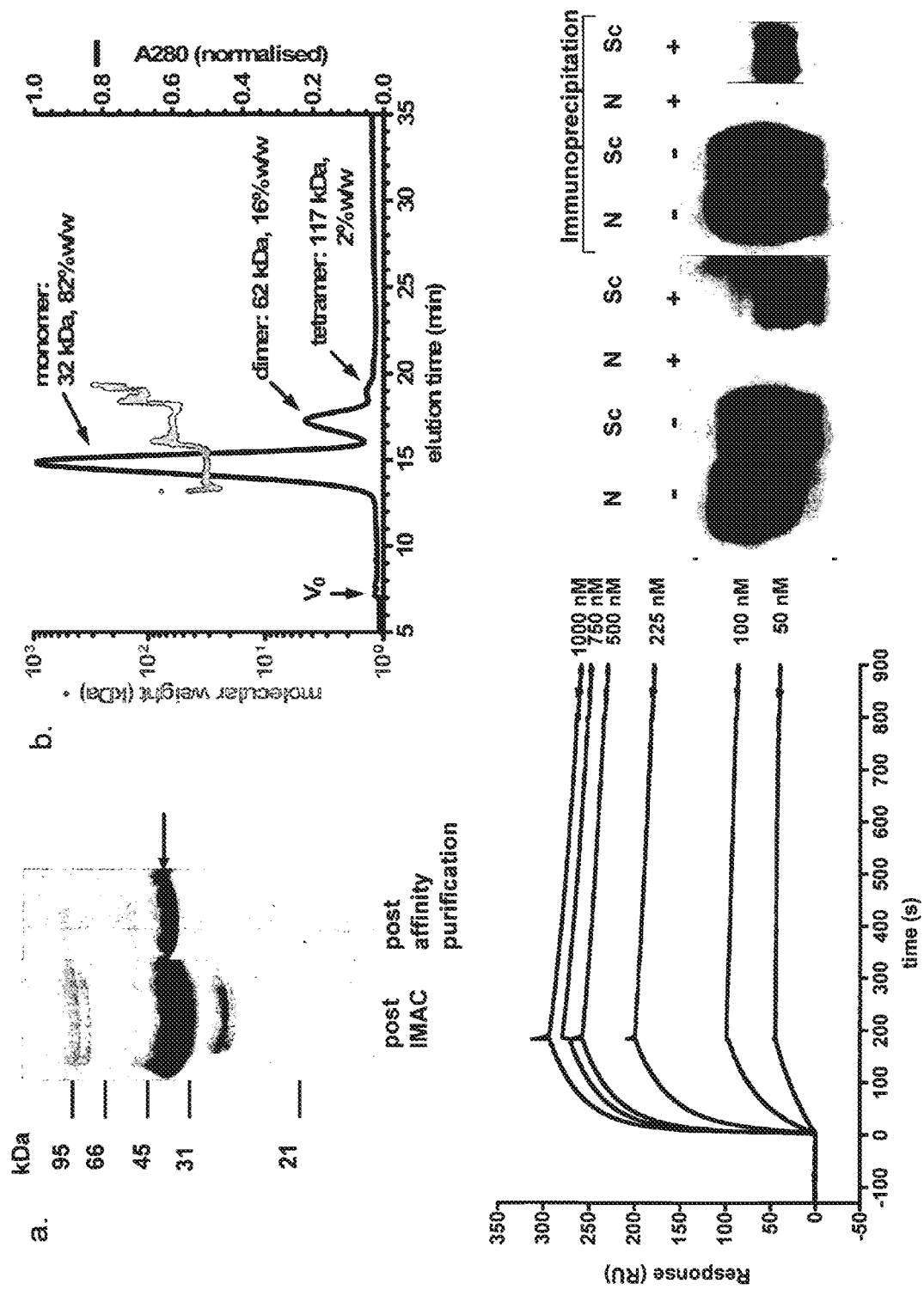

Under optimized conditions (see Materials and Methods), the expression yield was 10 mg soluble protein per liter of bacterial culture that were subsequently purified by IMAC (NiNTA, Qiagen, Germany) and affinity purification (sepharose column crosslinked with recombinant mouse PrP; FIG. 2a). The Far-UV circular dichroism spectrum of scFvW22 contained, like many scFvs (Pledger et al., 1999), mostly β-structure: a secondary structure estimate yielded 6% α-helix, 45% β-sheet, 11% β-turn and 39% unfolded structure (Lobley et al., 2002). Purified scFvW226 was mainly monomeric (85%, FIG. 2b) and the $K_D$ measured by SPR with recombinant mouse PrP was determined to be 2 nM, i.e. only four times lower than for the full length mAB (FIG. 2c). ScFvW226 retained binding activity to recombinant mouse PrP after incubation at 60° C. or in 90% serum at 37° C. for 72 h, indicating a high stability under physiological conditions. ScFvW226 retained the binding characteristics from its full length ancestor in that it immunoprecipitated both PrP$^C$ and PrP$^{Sc}$ from brain homogenates (FIG. 2d).

The epitope of scFvW226 was mapped to comprise the linear polypeptide sequence WEDRYYREN (residues 145-153) in helix 1 of PrP using a PepSpot library (Jerini Peptide Technology, Germany).

scFvW226 Antiprion Activity

Figure 3:
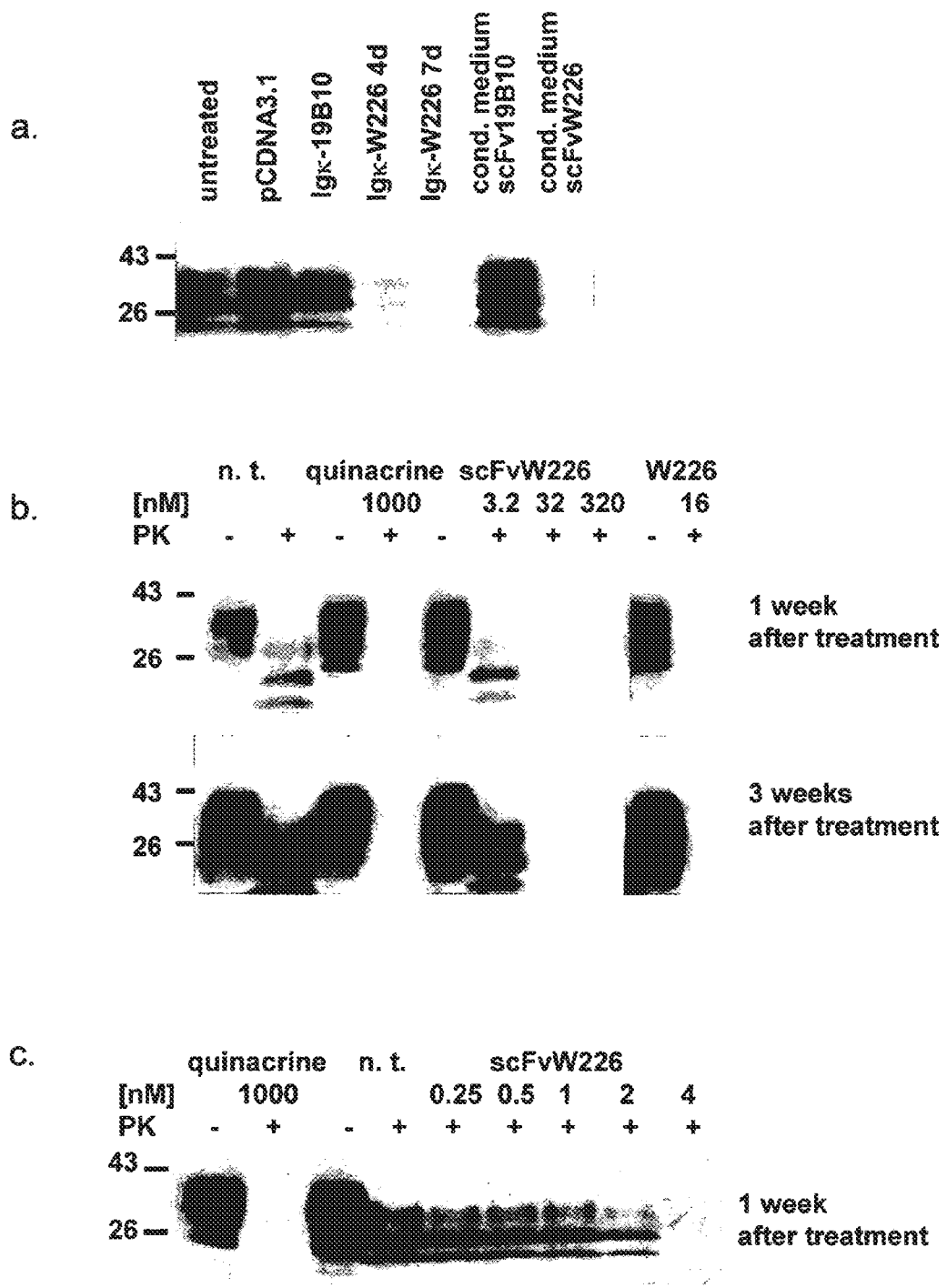

Next, scFvW226 was probed for antiprion activity. When scFvW226 cloned behind the IgGκ-signal sequence was transfected for secretion into ScN2a cells a clear time-dependent antiprion effect was observed (FIG. 3a; compare 4 days after transfection with 7 days after transfection). Similarly, when scFvW226 was expressed in non-infected N2a cells and the supernatant of the conditioned medium was transferred to untransfected ScN2a cells after four days, prions were cleared (FIG. 3a). A control scFv derived from an antibody recognizing only a subpopulation of PrP to be antiprion active.

When ScN2a cells were treated with purified scFvW226 generated in E. coli, prion-clearing effects within concentrations >3.2 nM (FIG. 3b) was observed. These antiprion effects were permanent since three weeks after discontinuation of scFvW226 administration, no PK-resistant immunoreactivity corresponding to PrP$^{Sc}$ reappeared (FIG. 3b, lower panel). The smallest effective concentration clearing prions from ScN2a cells as seen in Western blots was narrowed down to 4 nM (FIG. 3c).

When lysates of ScN2a cells treated with scFv for either ten days or three weeks were inoculated into tg20 indicator mice, scFvW226 concentrations as low as 10 nM were demonstrated to abolish prions from ScN2a cells (Table 1), thus confirming the results from the ScN2a cells.

Miniaturization of scFvW226

Figure 4:
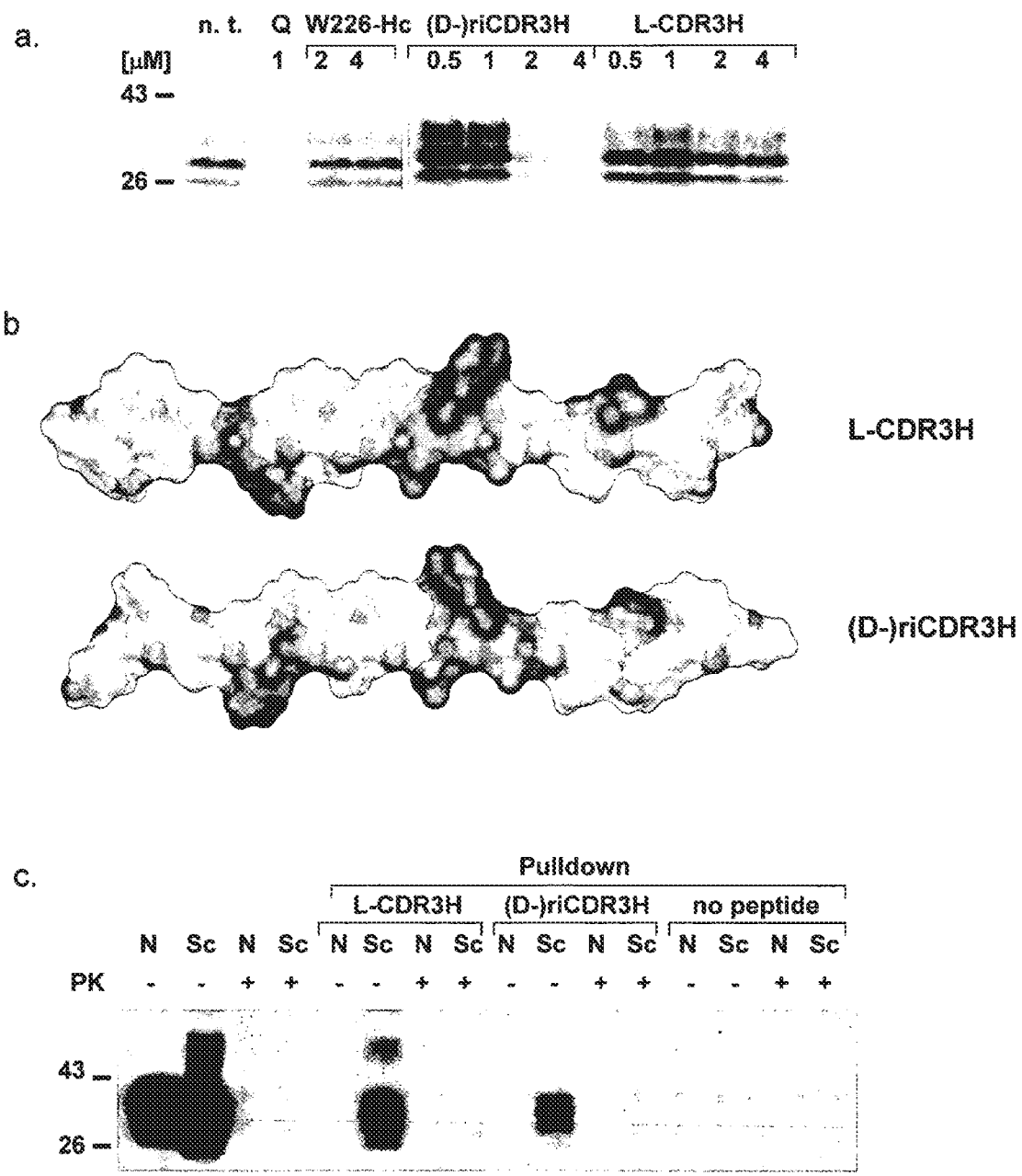

Smaller fragments than the combined CDR regions from heavy or light chain domains have sometimes shown full biological activity (Bourgeois et al., 1998; Colby et al., 2004; Jackson et al., 1999; Kim et al., 2006). For α-PrP antibodies, the heavy chain of mAB 6H4 has been shown to be sufficient for antiprion activity in vivo (Heppner et al., 2001). Cloning and expression of only the heavy chain variable domain of scFvW226 containing all three CDRs in E. coli, and administration to ScN2a cells failed to clear prions at concentrations where the entire scFvW226 would (FIG. 4a). When each of the CDRs were expressed as recombinant, cmyc- and His-tagged proteins in E. coli, the third CDR of the heavy chain domain (CDR3H), as well as the light chain exhibited weak binding to recombinant mouse PrP by an enzyme-linked immunosorbent assay.

TABLE 1

Bioassays of treated ScN2a cells in tg20 mice

| construct | number of ScN2a cells (×10⁵) | dosage of fragment [nM] | treatment time [days] | number of sick n/n₀ | incubation time [days] |
|---|---|---|---|---|---|
| PBS | 0.8 | — | 10 | 5/5 | 130 ± 20 |
| scW226 | 0.8 | 10 | 10 | 0/5 | |
| scW226 | 0.8 | 30 | 10 | 0/5 | |
| scFvW226 | 0.8 | 100 | 10 | 0/5 | |
| scFvW226 | 0.8 | 300 | 10 | 0/5 | |
| PBS | 2.8 | — | 21 d | 5/5 | 75 ± 2 |
| scFvW226 | 2.8 | 300 | 21 d | 0/5 | |
| W226-Hc | 2.8 | 300 | 21 d | 5/5 | 78 ± 3 |

ScN2a cells were treated with scFv in different concentrations, and for different times; even at the lowest concentration (10 nM) scFvW226 cleared prions completely.
PBS treatment (control) or treatment with 320 nM W226-Hc did not clear prions.

CDR3H is the most variable region among all CDRs (Shirai et al., 1996). In many antibodies, this region alone has been shown to exhibit weak binding to the epitope (Feng et al., 1998; Heap et al., 2005; Monnet et al., 1999). When the CDR3 heavy chain (CDR3H) was expressed in E. coli with a cmyc and His$_6$ tag or synthesized without the tags and administered to ScN2a cells, it exhibited no antiprion activity (FIG. 4a).

A Retro-Inverso (D-) Peptide of CDR3H is Antiprion Active

Retro-inverso D-peptide analogues of corresponding L-peptides are D-peptides ("inverso") in the reverse sequence order ("retro"), attempting to mimick the side chain topology of the L-peptide while having a different backbone with resistance to proteolysis by L-proteases in vivo. Binding of these peptides to the antigen would be predicted to occur only when the majority of binding interactions stems from side chain interactions rather than involving polypeptide backbone interactions. D-peptides offer advantages over L-peptides in that they have a dramatically increased half life time in vivo (Briand et al., 1995; Guichard et al., 1994; Levi et al., 2000). Surprisingly, the (D-)riCDR3H exhibited antiprion activity at concentrations of 4 µM where CDR3H had no activity (FIG.

4a). Attempts to measure different affinities of the peptides to PrP by SPR were limited due to the small molecular size of the peptides; the $K_D$s of both peptides has been estimated to be in the range of 1-10 μM, and no huge differences in the binding of the L- and the D-peptide could be observed.

Figure 5:
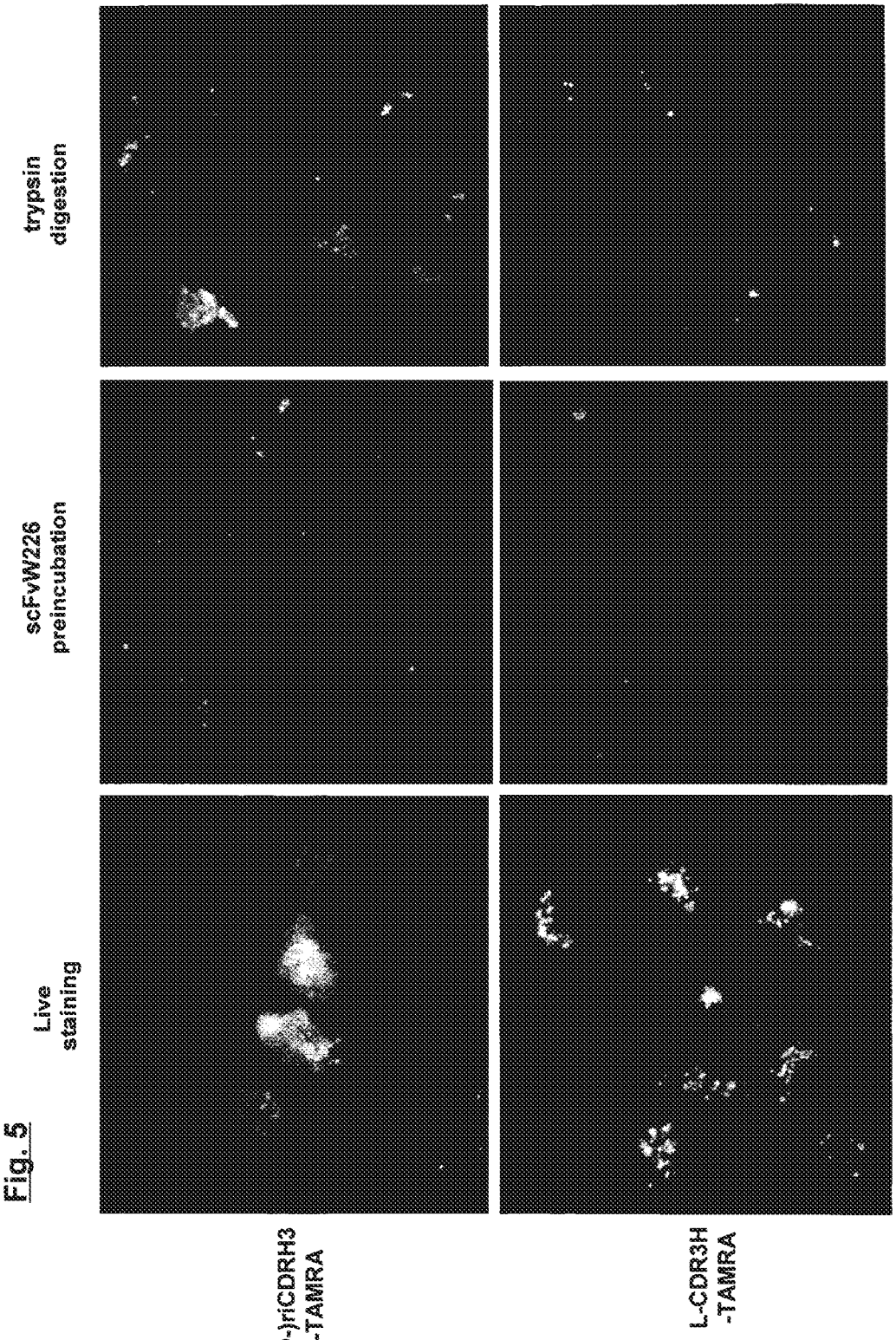

For further characterizing the differences that would be associated with differential antiprion activity of (D-) riCDR3H as opposed to CDR3H, live immunofluorescence stainings of ScN2a cells with TAMRA-labeled riCDR3H and CDR3H have been performed (FIG. 5). While riCDR3H exhibited staining all over the cell, CDR3H stained only intracellular compartments, likely after its endocytosis. Both stainings could be competed by scFvW226 indicating that both riCDR3H and CDR3H bound to the same antigens, i.e. PrP. As expected, only CDR3H could be digested by trypsin (FIG. 5). These findings indicated that the differential antiprion activity of riCDR3H was likely due to different in vivo characteristics that included half life time and subcellular targeting.

CDR3H and (D-)riCDR3H are Conformation-Specific Ligands for $PrP^{Sc}$

To investigate whether the CDR peptides had maintained PrP binding characteristics, pull down experiments with sepharose-immobilized peptides of brain homogenates from normal and RML-infected mice were performed. Surprisingly, CDR3H and (D-)riCDR3H pulled down only PrP from scrapie-infected homogenates that after digestion with PK revealed partial protease resistance indicating that this conformer was $PrP^{Sc}$ (FIG. 4c). Thus, compared to scFvW226, CDR3H peptides changed binding specificity and acquired conformation-specific binding to $PrP^{Sc}$, and this binding seemed side-chain mediated since both CDR3H and (D-)riCDR3H bound $PrP^{Sc}$, although the L-peptide a little stronger (FIG. 4c). The conformation-specificity of CDR3H and (D-)riCDR3H for $PrP^{Sc}$ could explain the difficulties of determining $K_D$s with recombinant mouse PrP which is though to resemble $PrP^C$ rather than $PrP^{Sc}$.

Use of scFvW226 or its Derivatives for Strain Specific Detection of Prions

Figure 7:
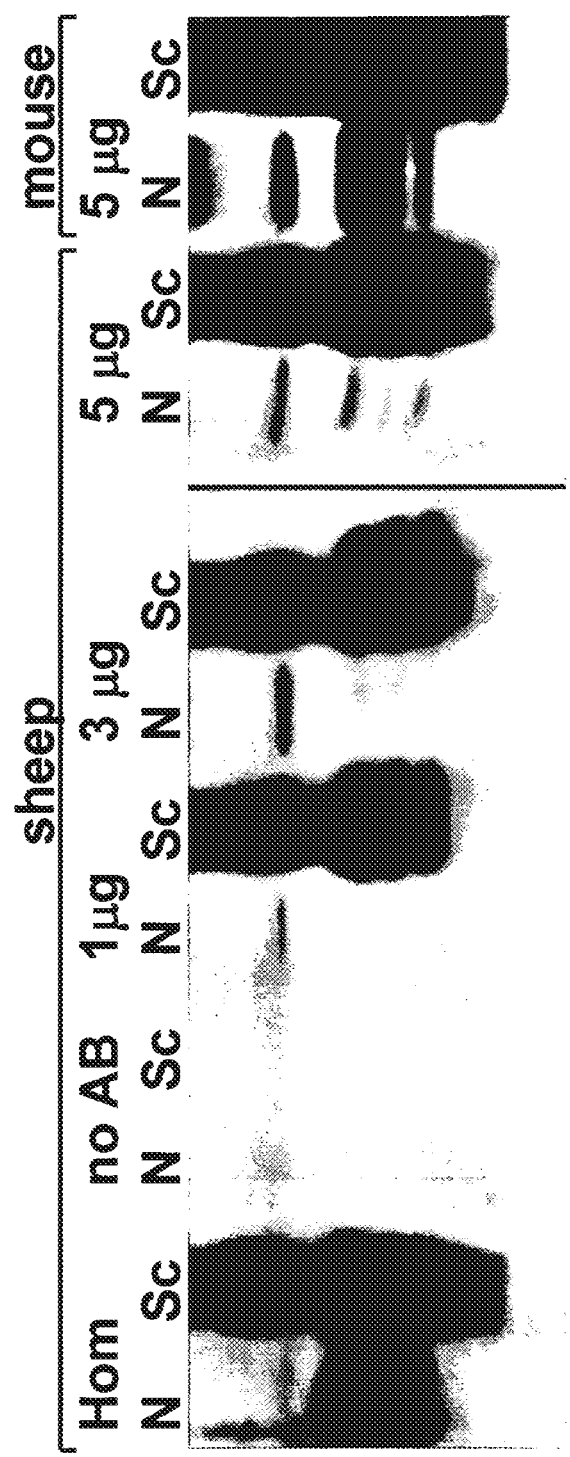

In FIG. 7 it is shown that not all prions ($PrP^{Sc}$) are recognized equally well by the W226 ligand. This characteristic may now be used to distinguish strains. For example, by using W226 traditional classic sheep scrapie may be distinguished from BSE scrapie, i.e. prions that originate from cattle infected with prions and transmitted to sheep. These prions are particularly dangerous for humans. Antibody fragments may be mutagenized at single amino acid residues to increase strain-specific recognition.

Use of scFvW226 or its Derivatives for Design and Construction of Fusion Proteins with Improved Diagnostics and Therapeutic Activity Using either the $PrP^C$ and $PrP^{Sc}$-recognizing scFvW226 or the $PrP^{Sc}$-specific CDR3H, fusion proteins can be made that facilitate diagnostics: horse radish peroxidase can be recombinantly fused to the gene of these antibody fragments and be used to detect prions enzymatically in a one-step reaction. Equally, these antibody fragments can be fused to enhanced fluorescent protein (EFP) or luciferase to directly attach a label. It may also be of advantage to add additional signal sequences to these antibody fragments allowing either improved passage through the blood-brain barrier and/or arrival at particular CNS structures. It is also conceivable to add signal sequences or cell transduction sequences allowing the recombinant antibody fragment to reach defined cellular compartments. The antibody fragments may also be recombinantly combined with each other to yield antibody fragments of variable size capable of binding PrP at multiple sites. This may lead to decreased dissociation of the antibody fragment from PrP due to increased avidity. These constructs may be particularly useful for immunization experiments. It is also conceivable to combine scFvW226-derived antibody fragments with other recombinant antibodies or protein ligands by construction respective fusion proteins; these may be advantageous since they combine the bioavailability characteristics of both fragments.

Anti-Idiotypic Antibodies to scFvW226 (CDR3H) Bind PrP

The epitopes of full length mAB W226 and scFvW226 were mapped to helix 1 of the prion protein (residues WEDRYYREN). Since helix 1 is known to be an interaction site in the $PrP^C/PrP^{Sc}$ complex (Solforosi et al., 2007), the minimal PrP-binding domain within scFvW226, the complementarity-determining region (CDR) 3 of the heavy chain (CDR3H) was used in an immunization experiment in order to generate anti-idiotypic antibodies to PrP. These anti-CDR3H antibodies should ultimately resemble the PrP helix 1 domain and therefore be able to bind to PrP.

Wild type 129 SvEv mice have been immunized with recombinantly expressed CDR3H or synthesized riCDR3H crosslinked to KLH with Linaris adjuvant (in both cases a total of 3 boosters over 10 weeks), and generated hybridoma of their spleens by standard methods. For the mouse immunized with CDR3H, 28 hybridoma secreting monoclonal antibodies (mABs) recognizing both the immunogen and mouse PrP were generated; 8 clones were generated that only recognized the immunogen. The anti-PrP mABs had different characteristics in that by immunoprecipitation they recognized $PrP^C$ and $PrP^{Sc}$, only $PrP^C$ or only $PrP^{Sc}$. One clone from this fusion is mAB 7A7. This antibody was able to immunoprecipitate specifically $PrP^{Sc}$.

This novel method of generating anti-PrP mABs overcame the state of prior art and the previous notion that an effective immune response against PrP was impossible in wild type animals due to self tolerance. The present invention comprises therefore immunization with an antibody or antibody fragment binding to an interaction domain of PrP and using it as an immunogen to circumvent self tolerance to this antigen.

Immunizing a mouse with chemically synthesized riCDR3H crosslinked to keyhole limpet hemocyanin (KLH) by a similar protocol as described above and fusing the spleen to generate hybridoma by standard methods, equally resulted in anti-PrP antibodies of differential conformation specificity. Thus, the riCDR3H is able to overcome self tolerance of humoral immune response against PrP.

In order to demonstrate that this active immunization strategy could be used to protect from prion infection, five CD1 mice were immunized four times in 2 week intervals with CDR3H peptide produced in and purified from E. coli, with the first two immunizations utilizing ABM-ZK adjuvant (Linaris, Germany) and the last two boosts with ABM-N (Linaris, Germany) as adjuvant. These five mice as well as five non-immunized controls were then inoculated intraperitoneally with a 10-4 dilution of a proven 10% homogenate scrapie (RML) infected terminally sick mouse brain in PBS (20 micL/mouse). Control mice died with an average incubation time of 195 days. From the immunized mice, one mouse survived (>10 months), whereas the other four died with an average incubation time of 205 days. Thus, CDR3H is able to protect from prion disease. These immunization procedures can be further improved by providing immunogens where several CDR3H fragments are cloned behind each other resulting in double, triple, or multiple identical sites of the immunogen in one protein. These repetitive structures may particularly well be recognized by the immune processing machinery and lead to an increased anti-PrP immune response. Similarly, riCDR3H can be chemically crosslinked to a D-peptide scaffold to result in a multiple antigenic peptide (MAP). This MAP equally presents a repetitive structure favoring a strong anti-PrP immune response.

Antiprion Activity of scFvW226 in Prion-Infected Mice

In order to demonstrate therapeutic effects of a passive immunization strategy with scFvW226 against ongoing prion disease, an experiment was set up where C57/B6 mice were inoculated intraperitoneally with a 10-3 dilution of a proven 10% homogenate scrapie (RML) infected terminally sick mouse brain in PBS (20 micL/mouse). Thirty days after inoculation, intraperitoneal treatment with either full length purified mABW226 or scFvW226 was started. Nine untreated controls, and five mice treated with either mABW226 2 mg/mouse or 1 mg scFvW226/mouse twice a week for an unlimited period. There had been a steady loss of weight for the control mice prior to scrapie sickness, whereas none of the treated mice experienced any weight loss. There was a significant effect on increasing the survival time by administration of scFvW226 or full length antibody. This experiment proved that scFvW226 (or mABW226) was able to prevent prion disease when given after inoculation.

Immunostimulatory Effect of mAB W226 and scFvW226

To investigate whether scFv W226 or full length mAB W226 had effects on the T cell immune response, T cells were isolated from a transgenic mouse expressing T cell receptor specific for myelin basic protein (MBP). These T cells would specifically proliferate upon encountering MBP 1-11 antigen, a peptide comprising the N-terminal first eleven residues of MBP. It could be demonstrated that addition of scFvW226 (A.) or mAB W226 (B.) increased T cell proliferation in the presence of MBP 1-11 indicating that scFvW226 or mAB W226 have immunostimulating effects.

Thus, the potential application of scFvW226 or its derivatives is also to counteract immunosuppressed conditions like aplastic anemia, leukemias, or HIV/AIDS, or others, or as immunoadjuvant when the immune response in individuals is weakened, for example in older patients receiving active immunizations.

TABLE 2

Mutagenesis of CDR3H

| No. | Peptide | Sequence | Specificity | Affinity |
|---|---|---|---|---|
| 1. | LH3 | YFCARWNWERDAMDYWG (SEQ ID NO: 1) | $PrP^{Sc}$ | 0 |
| 2. | LH3A3 | YFAARWNWERDAMDYWG (SEQ ID NO: 14) | $PrP^{Sc}$ | |
| 3. | LH3A5 | YFCAAWNWERDAMDYWG (SEQ ID NO: 15) | $PrP^{Sc}$ | |
| 4. | LH3A6 | YFCARANWERDAMDYWG (SEQ ID NO: 16) | $PrP^{Sc}$ | |
| 5. | LH3A7 | YFCARWAWERDAMDYWG (SEQ ID NO: 17) | $PrP^{Sc}$ | (+) |
| 6. | LH3A8 | YFCARWNAERDAMDYWG (SEQ ID NO: 18) | $PrP^{Sc}$ | |
| 7. | LH3A9 | YFCARWNWARDAMDYWG (SEQ ID NO: 19) | $PrP^{Sc}$ | |
| 8. | LH3A10 | YFCARWNWEADAMDYWG (SEQ ID NO: 13) | $PrP^{C}$ | |

TABLE 2-continued

Mutagenesis of CDR3H

| No. | Peptide | Sequence | Specificity | Affinity |
|---|---|---|---|---|
| 9. | LH3A11 | YFCARWNWERAAMDYWG (SEQ ID NO: 20) | $PrP^{Sc}$ | |
| 10. | LH3A13 | YFCARWNWERDAADYWG (SEQ ID NO: 11) | $PrP^{Sc}$ | + |
| 11. | LH3A14 | YFCARWNWERDAMAYWG (SEQ ID NO: 21) | $PrP^{Sc}$ | (+) |
| 12. | LH3A15 | YFCARWNWERDAMDAWG (SEQ ID NO: 22) | $PrP^{Sc}$ | |
| 13. | LH3D5 | YFCADWNWERDAMDYWG (SEQ ID NO: 23) | $PrP^{Sc}$ | (-) |
| 14. | LH3R9 | YFCARWNWRRDAMDYWG (SEQ ID NO: 24) | $PrP^{Sc}$ | (+) |
| 15. | LH3D10 | YFCARWNWEDDAMDYWG (SEQ ID NO: 25) | $PrP^{Sc}$ | (+) |
| 16. | LH3R11 | YFCARWNWERRAMDYWG (SEQ ID NO: 12) | $PrP^{Sc}$ | + |
| 17. | LH3R14 | YFCARWNWERDAMRYWG (SEQ ID NO: 26) | $PrP^{Sc}$ | |

In the peptides, for each subsequent residue, the amino acid was substituted with an alanine, that is thought to abrogate side chain interactions but maintain secondary structure (Nos. 1-12). Evaluation was done by comparing the specificity and affinity for PrPSc pulldown to that of peptide LH3 (CDR3H).

Mutagenesis of CDR3H

Table 2 shows a mutagenesis experiment of peptides derived from SEQ ID NO:1 (CDR3H, here termed LH3). In the derived peptides, for each subsequent residue, the amino acid was substituted with an alanine (Nos. 1-12), that is thought to abrogate side chain interactions but maintain secondary structure. Further substitutions have also been accomplished as shown in Table 2 (Nos. 13-17). Evaluation was done by comparing the specificity and affinity for $PrP^{Sc}$ pull-down to that of peptide LH3 (CDR3H, SEQ ID NO:1). There are three remarkable results that serve to further narrow the role of side chains of the LH3 peptide in $PrP^{Sc}$ (prion-) specificity:

1. Mutagenesis of R10 to A10 (No. 8: LH3A10, SEQ ID NO: 13) abrogates $PrP^{Sc}$ specificity: this peptide binds to $PrP^{C}$.

2. The two changes M13A (No. 10: LH3A13, SEQ ID NO:11) and D11R (No. 16: LH3R11, SEQ ID NO:12) increase affinity for $PrP^{Sc}$.

3. Changes at residues N7A (No. 5: LH3A7, SEQ ID NO:17), D14A (No. 11: LH3A14, SEQ ID NO: 21), E9R (No. 14: LH3R9, SEQ ID NO:24), R10D (No. 15: LH3D10, SEQ ID NO:25) slightly increase affinity for $PrP^{Sc}$ whereas change R5D (No. 13: LH3D5, SEQ ID NO:23) slightly decreases affinity for $PrP^{Sc}$.

Exemplary Materials and Methods

Constructs

W226 hybridoma secreting IgGl mAB and recognizing both $PrP^{C}$ and $PrP^{Sc}$ had been generated by standard fusion procedure of myeloma cells with splenocytes from a PrP knockout mouse (Büeler et al., 1992) immunized with purified mouse $PrP^{Sc}$. To prepare a single chain Fv construct (scFv), mRNA purified from W226 hybridoma was used for PCR amplification with the following primer set: 5'-AAAACCATGGCGGAGGTCCAGCTGCAGCAGTC (SEQ ID NO:27) 3' ($V_H$ forward) and 5'-TTTTGCCGGCCAGTG- GATAGTCAGATGGGGGTGTCGTTTTGGC (SEQ ID NO:28)-3' ($V_H$ reverse) or 5'-AAAGGATCCGACATTGT-GATGACCCAGTCT (SEQ ID NO:29)-3 ($V_L$ forward) and 5'-AAAAGCGGCCGCGGATACAGTTGGTGCAGCATC (SEQ ID NO:30)-3' ($V_L$ reverse). PCR products were digested with NgoM IV ($V_H$) or BamHl ($V_L$) and ligated to the NgoMlV and BamHl site of a linker oligonucleotide coding for a (Gly$_4$Ser)$_3$ linker domain (Huston et al., 1988). An 800 by fragment corresponding to the correct ligation product was eluted from an agarose gel and amplified using the $V_H$ forward and $V_L$ reverse primer. The product was cut with Ncol and Eagl and ligated into the procaryotic expression vector pET22b (Novagen), allowing the expression with an N-terminal pelB leader sequence and a c-terminal His$_6$-tag (see FIG. 1). In addition a c-myc-tag was cloned into the Eagl/Xhol sites between the scFv and the His$_6$-tag. For construction of only the heavy chain domain (W226-Hc), $V_H$ was amplified with appropriate primers allowing the cloning via Ncol and Eagl into pET22b-Myc/His$_6$. For eukaryotic expression of scFvW226, the combined scFvW226 cDNA was amplified with a 5'-primer including a IgGK-leader sequence (Donofrio et al., 2005) and ligated via HindIII/EcoRl (W226) into pCDNA3.1 (Invitrogen).

Peptides

CDR3H corresponding to the sequence NH2-YFCARWN-WERDAMDYWG (SEQ ID NO: 1, one letter amino acid code)-COOH and the retro-inverso D-peptide [(D-)riCDR3H] corresponding to the sequence NH2-gwydma-drewnwracfy (SEQ ID NO:2, one letter amino acid code, small letter convention for D-peptides)-COOH were synthesized either unlabeled or N-terminally linked to 6-Carboxytetramethylrhodamine (TAMRA) by JPT Peptide Technology (Berlin, Germany).

Protein Expression and Purification

Expression of scFvW226 or W226-Hc was induced in BL21 (λDE3) Rosetta (EMD, Novagen Brand, Madison, Wis.): bacteria were grown at 37° C. to high density (OD$_{600}$>2.0) in a 2 L-fermenter (MoBiTec, Göttingen, Germany) and cooled down on ice before induction with 0.5 mM IPTG at 15° C. over night. Cell pellets were lyzed in 20 mM Tris pH 8.0, 1% T-X100, 500 mM NaCl, 5 mM imidazole, 20 mM MgCl$_2$, 1 mM PMSF, 1 mg/ml lysozyme and 500U DNase. Lysates were cleared by centrifugation and soluble protein in the supernatant was purified via Ni-NTA columns (Qiagen, Hilden, Germany). After loading, the column was washed with 10 column volumes (CV) 20 mM Tris pH8.0, 500 mM NaCl, 1% TX-100, 5 mM imidazole, 10 CV 20 mM Tris pH8.0, 500 mM NaCl, 1% TX-100, 20 mM imidazole and 10 CV 20 mM Tris pH 8.0, 1000 mM NaCl, 5 mM imidazole. Bound proteins were eluted with 20 mM Tris pH 8.0, 300 mM NaCl, 300 mM imidazole yielding a purity of about 60% for scFvW226 and 90% for W226-Hc. Eluted scFvW226 was further purified to >95% purity by affinity chromatography employing recombinant mouse PrP (Korth et al., 1999) coupled to NHS-Sepharose (Amersham) according to manufacturer's recommendations. From the affinity column, scFvW226 was eluted with 100 mM glycine pH 2.5 and immediately neutralized with 100 mM Tris pH 8.8. Finally, purified antibody fragments were dialyzed twice against PBS. The mass of scFvW226 was measured by mass pectromtery and found to be identical to the calculated one.

Pull-Down Experiments scFvW226, W226-Hc, riCDR3H and CDR3H were coupled to NHS-sepharose. 10% mouse brain homogenates prepared from C57BL/6 or RML-infected C57BL/6 mice (Chandler, 1961) were diluted 1:10 in in 20 mM Tris HCl pH 8.0, 150 mM NaCl, 0.3% sarcosyl and precleared by centrifugation for 15 min at 22.000×g. 1 mL thereof was incubated with 20 µL of loaded beads at 4° C. over night. In a positive control experiment, 5 µg of recombinant mouse PrP in the same buffer was used. After incubation, beads were washed twice in IP1-buffer (50 mM Tris pH7.5, 150 mM NaCl, 1% NP40, 0.5% DOC), IP2-buffer (50 mM Tris pH 7.5, 500 mM NaCl, 0.1% NP40, 0.05% DOC) and IP3-buffer (50 mM Tris pH7.5, 0.1% NP40, 0.05% DOC). Where necessary, beads were also incubated with 4 µg Proteinase K (Merck, Darmstadt, Germany) in 20 µL IP3 buffer prior elution of bound PrP with 2× loading buffer at 95° C. The eluates were separated on a 4%-20%-Tris HCl gel (Biorad, USA) and PrP was detected by Western Blot using mAb W226.

Circular Dichroism (CD) Analyses

Far-UV CD spectra (195-250 nm) were recorded using a Jasco J-810 spectrometer. Sample conditions: 3 µM protein in 20 mM NaPO$_4$ pH 7.5, 0.2 mM EDTA at room temperature (2 mm cuvette). Scan conditions: 20 nm/min scan speed, 100 mdeg sensitivity, 0.2 nm pitch, 1 nm band width, 2 s response time, 40 accumulations.

Asymmetric Field-Flow Fractionation (aFFF)

System: Eclipse 2 equipped with HELEOS, Optilab Rex (Wyatt Technologies, USA) and a multiple wavelength detector (Agilent, USA). Software: Eclispe 2.5 and Astra 5.3.1.4. Conditions: scFvW226 was separated in 10 mM Tris-HCl pH 8, 50 mM NaCl, 1 mM EDTA with a 1 ml/min channel flow, using a 490 µm spacer and 5 kDa MWCO cellulose membrane. Flow scheme: sample inject (50 µL/75 µg)→focussing (2 min, 3 mL/min cross-flow ($V_x$))→$1^{st}$ elution phase (20 min, 2 mL/min linear $V_x$)→$2^{nd}$ phase (5 min 2.0-0.15 mL/min $V_x$ gradient)→$3^{rd}$ phase (5 min $V_x$ off).

Surface Plasmon Resonance Analysis (SPR)

Binding kinetics were determined on a Biacore 1000 (Biacore AB, Uppsala, Sweden). Recombinant mouse PrP (1 µM) was diluted in 10 mM NaOAc pH 4.5 and immobilized on a EDC/NHS activated CM5-chip (Biacore) at 5 µl/min. After immobilization and blocking with ethanolamine, the chip was washed with 50 mM NaOH until a steady signal was obtained. Final surface density was about 2000 RU. All kinetic SPR analysis were run at 5 µl/min PBS flow and antibody fragments were injected at different concentrations ranging from x to y nM. Association and dissociation was recorded for 180 s respectively. After each cycle, the surface was regenerated with a x s pulse of 50 mM NaOH. Kinetic data were calculated using BIAevaluation 4.1 software according to a 1:1 (Langmuir) binding model.

PrP$^{Sc}$ Inhibition Assay

Inhibition by Purified Antibody Fragments

ScN2a cells (Bosque and Prusiner, 2000; Butler et al., 1988) were grown in MEM, supplemented with 2 mM L-glutamine, 100 U/mL penicillin, 100 µg/mL streptomycin and 10% FCS. For treatment, ScN2a cells were seeded in 60 mm dishes and incubated with antibody fragments for 7 days. After 3 days, medium/antibody fragments were changed. Cells were lyzed in 500 µL lysis buffer (50 mM Tris HCl pH8.0, 150 mM NaCl, 0.5% T-X100, 0.5% DOC) and equal amounts of lysates were treated with Proteinase K (20 µg/mL) for 30 min at 37° C. After stopping protease digestion with 100 µM PMSF, PrP$^{Sc}$ in 400 µL lysis buffer was pelleted at 100.000×g in a TLA-55 rotor in a n Optima ultracentrifuge (BeckmanCoulter, USA). PrP$^{Sc}$ was detected after separation on a 4%-20% Tri-HCl gel (Biorad, USA) by Western Blot using mAb W226.

Inhibition by Antibody Fragments Expressed in Cells

ScN2a cells were splitted in 60 mm dishes the day before transfection to obtain 50% confluency and 1.3 µg pcDNA plasmid encoding scFvW226 or control scFv was transfected with HiPerfect (Qiagen, Germany) according to manufacturer's instructions. After four days cells either were lyzed and analyzed for PrP$^{Sc}$ as described above or they were transferred to a 100 mm dish and incubated for additional 3 days before lysis. In addition, non-infected N2a cells were transfected in the described way and, after four days, conditioned medium was transferred to freshly seeded ScN2a cells, which subsequently were incubated for another four days.

Bioassay

Two separate treatment experiments of determining the presence of prions after scFvW226 or full length mAB W226 treatment by inoculation in tg20 mice (Fischer et al., 1996) were performed: ScN2a cells were grown in 60 mm dishes and treated with 10 nM, 30 nM, 100 nM or 300 nM for 10 days with two splittings and scFvW226 renewals. In a second experiment, ScN2a cells grown in 60 mm dishes and treated with either 320 nM W226-scFv or W226-Hc. After three weeks of treatment, including two passages, cells were collected by scraping, washed in PBS, counted and resuspended in 100 μl PBS, followed by five cycles of freeze/thawing. For both experiments, 20 μl of lysates corresponding to 0.8 or 2.8×10e5 cells were injected i.c. into five tg20 mice for each treatment condition.

ScN2a Cell Immunofluorescence Staining

Live ScN2a cells were washed with PBS and, in one condition, preincubated with medium containing 100 μM scFvW226 for 30 min at RT. Subsequently, 1 μM of undigested or trypsin-digested TAMRA-labeled riCDR3H or CDR3H was added. Trypsin-digestion was carried out with 100 μg trypsin for 3 h at 37° C. After incubation with labeled peptides of 3 h, cells were fixed with 4% paraformaldehyde and washed three times with PBS before inspection.

The prion protein, PrP, exists in several stable conformations, with the presence of one conformation, PrP$^{Sc}$, associated to transmissible neurodegenerative diseases. Targeting PrP by high-affinity ligands has been proven an effective way of preventing peripheral prion infections. Here, recombinant single chain fragments of the variable domains (scFv) of a monoclonal antibody have been generated in *E. coli*, originally raised against purified PrP$^{Sc}$ and recognizing both PrP$^{C}$ and PrP$^{Sc}$. This scFv fragment had a dissociation constant ($K_D$) with recombinant PrP of 2 nM and cleared prions in ScN2a cells at 4 nM, as demonstrated by bioassay. Recombinant expression of only its complementarity determining region 3 of the heavy chain (CDR3H) led to conformation-specific recognition of only $PrP^{Sc}$ in solution, however, antiprion activity was lost. Synthesis of a retro-inverso D-peptide of CDR3H reinstated antiprion activity. Thus, 1. scFvW226 is so far the smallest polypeptide with bioassay proven antiprion activity and 2. differential conformation-specificity can be regulated by orchestrating the participation of different CDRs.

Mutagenesis Experiments

Peptides were synthesized by JPT Peptides (Berlin, Germany) at >70% purity and HPLC purified. Peptides were coupled to NHS sepharose via their free N-terminal amine and used in a pull-down experiment as described above. Evaluation was then done by comparing the specificity and affinity for PrPSc pulldown to peptide CDR3H (also termed LH3). The results of this investigation are listed in Table 2.

REFERENCES

Bard F., Cannon C., Barbour R., Burke R. L., Games D., Grajeda H., Guido T., Hu K., Huang J., Johnson-Wood K., Khan K., Kholodenko D., Lee M., Lieberburg I., Motter R., Nguyen M., Soriano F., Vasquez N., Weiss K., Welch B., Seubert P., Schenk D. and Yednock T. (2000) Peripherally administered antibodies against amyloid beta-peptide enter the central nervous system and reduce pathology in a mouse model of Alzheimer disease. *Nat. Med.* 6, 916-9.

Bosque P. J. and Prusiner S. B. (2000) Cultured cell sublines highly susceptible to prion infection. *J. Virol.* 74, 4377-4386.

Bourgeois C., Bour J. B., Aho L. S. and Pothier P. (1998) Prophylactic administration of a complementarity-determining region derived from a neutralizing monoclonal antibody is effective against respiratory syncytial virus infection in BALB/c mice. *J. Virol.* 72, 807-10.

Briand J. P., Guichard G., Dumortier H. and Muller S. (1995) Retro-inverso peptidomimetics as new immunological probes. Validation and application to the detection of antibodies in rheumatic diseases. *J. Biol. Chem.* 270, 20686-91.

Büeler H., Fisher M., Lang Y., Bluethmann H., Lipp H.-P., DeArmond S. J., Prusiner S. B., Aguet M. and Weissmann C. (1992) Normal development and behaviour of mice lacking the neuronal cell-surface PrP protein. *Nature* 356, 577-582.

Butler D. A., Scott M. R. D., Bockman J. M., Borchelt D. R., Taraboulos A., Hsiao K. K., Kingsbury D. T. and Prusiner S. B. (1988) Scrapie-infected murine neuroblastoma cells produce protease-resistant prion proteins. *J. Virol.* 62, 1558-1564.

Chandler R. L. (1961) Encephalopathy in mice produced by inoculation with scrapie brain material. *Lancet* 1, 1378-9.

Colby D. W., Garg P., Holden T., Chao G., Webster J. M., Messer A., Ingram V. M. and Wittrup K. D. (2004) Development of a human light chain variable domain (V(L)) intracellular antibody specific for the amino terminus of huntingtin via yeast surface display. *J. Mol. Biol.* 342, 901-12.

Donofrio G., Heppner F. L., Polymenidou M., Musahl C. and Aguzzi A. (2005) Paracrine inhibition of prion propagation by anti-PrP single-chain Fv miniantibodies. *J. Virol.* 79, 8330-8.

Feng Y., Chung D., Garrard L., McEnroe G., Lim D., Scardina J., McFadden K., Guzzetta A., Lam A., Abraham J., Liu D. and Endemann G. (1998) Peptides derived from the complementarity-determining regions of anti-Mac-1 antibodies block intercellular adhesion molecule-1 interaction with Mac-1. *J. Biol. Chem.* 273, 5625-30.

Fischer M., Rülicke T., Raeber A., Sailer A., Moser M., Oesch B., Brandner S., Aguzzi A. and Weissmann C. (1996) Prion protein (PrP) with amino-proximal deletions restoring susceptibility of PrP knockout mice to scrapie. *EMBO J.* 15, 1255-1264.

Goodrich J. A. and Kugel J. F. (2006) *Binding and Kinetics for Molecular Biologists*. Cold Spring Harbor Press, Cold Spring Harbor, N.Y.

Guichard G., Benkirane N., Zeder-Lutz G., van Regenmortel M: H., Briand J. P. and Muller S. (1994) Antigenic mimicry of natural L-peptides with retro-inverso-peptidomimetics. *Proc. Natl. Acad. Sci. USA* 91, 9765-9.

Heap C. J., Wang Y., Pinheiro T. J., Reading S. A., Jennings K. R. and Dimmock N. J. (2005) Analysis of a 17-amino acid residue, virus-neutralizing microantibody. *J. Gen. Virol.* 86, 1791-800.

Heppner F. L., Musahl C., Arrighi I., Klein M. A., Rulicke T., Oesch B., Zinkernagel R. M., Kalinke U. and Aguzzi A. (2001) Prevention of scrapie pathogenesis by transgenic expression of anti-prion protein antibodies. *Science* 294, 178-82.

Huston J. S., Levinson D., Mudgett-Hunter M., Tai M. S., Novotny J., Margolies M. N., Ridge R. J., Bruccoleri R. E., Haber E., Crea R. and et al. (1988) Protein engineering of antibody binding sites: recovery of specific activity in an anti-digoxin single-chain Fv analogue produced in Escherichia coli. Proc. Natl. Acad. Sci. USA 85, 5879-83.

Jackson N. A., Levi M., Wahren B. and Dimmock N. J. (1999) Properties and mechanism of action of a 17 amino acid, V3 loop-specific microantibody that binds to and neutralizes human immunodeficiency virus type 1 virions. J. Gen. Virol. 80 (Pt 1), 225-36.

Kayed R., Head E., Thompson J. L., McIntire T. M., Milton S. C., Cotman C. W. and Glabe C. G. (2003) Common structure of soluble amyloid oligomers implies common mechanism of pathogenesis. Science 300, 486-9.

Kim Y. R., Kim J. S., Lee S. H., Lee W. R., Sohn J. N., Chung Y. C., Shim H. K., Lee S. C., Kwon M. H. and Kim Y. S. (2006) Heavy and light chain variable single domains of an anti-DNA binding antibody hydrolyze both double- and single-stranded DNAs without sequence specificity. J. Biol. Chem. 281, 15287-95.

Korth C., Stierli B., Streit P., Moser M., Schaller O., Fischer R., Schulz-Schaeffer W., Kretzschmar H., Raeber A., Braun U., Ehrensperger F., Hornemann S., Glockshuber R., Riek R., Billeter M., Wuthrick K. and Oesch B. (1997) Prion ($PrP^{Sc}$)-specific epitope defined by a monoclonal antibody. Nature 389, 74-77.

Korth C., Streit P. and Oesch B. (1999) Monoclonal antibodies specific for the native, disease-associated isoform of the prion protein. Methods Enzymol. 309, 102-112.

Kuhn F., Purro M., Schmid J., Roller M., Lohmann C., Oesch B. and Raeber A. (2005) Detection of PrPSc by FACS using the prion specific antibody 15B3. In Prion 2005. Between fundamentals and society's needs., p. 193, Duesseldorf.

Lau A. L., Yam A. Y., Michelitsch M. M., Wang X., Gao C., Goodson R. J., Shimizu R., Timoteo G., Hall J., Medina-Selby A., Coit D., McCoin C., Phelps B., Wu P., Hu C., Chien D. and Peretz D. (2007) Characterization of prion protein (PrP)-derived peptides that discriminate full-length PrPSc from PrPC. Proc. Natl. Acad. Sci. USA 104, 11551-6.

Leliveld S. R. and Korth C. (2007) The use of conformation-specific ligands and assays to dissect the molecular mechanisms of neurodegenerative diseases. J. Neurosci. Res. 85, 2285-97.

Lesne S., Koh M. T., Kotilinek L., Kayed R., Glabe C. G., Yang A., Gallagher M. and Ashe K. H. (2006) A specific amyloid-beta protein assembly in the brain impairs memory. Nature 440, 352-7.

Levi M., Hinkula J. and Wahren B. (2000) A retro-inverso miniantibody with anti-HIV activity. AIDS Res. Hum. Retroviruses 16, 59-65.

Lobley A., Whitmore L. and Wallace B. A. (2002) DICHROWEB: an interactive website for the analysis of protein secondary structure from circular dichroism spectra. Bioinformatics 18, 211-2.

Luibl V., Isas J. M., Kayed R., Glabe C. G., Langen R. and Chen J. (2006) Drusen deposits associated with aging and age-related macular degeneration contain nonfibrillar amyloid oligomers. J. Clin. Invest. 116, 378-85.

Monnet C., Laune D., Laroche-Traineau J., Biard-Piechaczyk M., Briant L., Bes C., Pugniere M., Mani J. C., Pau B., Cerutti M., Devauchelle G., Devaux C., Granier C. and Chardes T. (1999) Synthetic peptides derived from the variable regions of an anti-CD4 monoclonal antibody bind to CD4 and inhibit HIV-1 promoter activation in virus-infected cells. J. Biol. Chem. 274, 3789-96.

Moroncini G., Kanu N., Solforosi L., Abalos G., Telling G. C., Head M., Ironside J., Brockes J. P., Burton D. R. and Williamson R. A. (2004) Motif-grafted antibodies containing the replicative interface of cellular PrP are specific for PrPSc. Proc. Natl. Acad. Sci. USA 101, 10404-9.

Nazor K. E., Kuhn F., Seward T., Green M., Zwald D., Purro M., Schmid J., Biffiger K., Power A. M., Oesch B., Raeber A. J. and Telling G. C. (2005) Immunodetection of disease-associated mutant PrP, which accelerates disease in GSS transgenic mice. EMBO J. 24, 2472-80.

Norstrom E. M. and Mastrianni J. A. (2006) The charge structure of helix 1 in the prion protein regulates conversion to pathogenic PrPSc. J. Virol. 80, 8521-9.

Pace C. N., Vajdos F., Fee L., Grimsley G. and Gray T. (1995) How to measure and predict the molar absorption coefficient of a protein. Protein Sci. 4, 2411-23.

Paramithiotis E., Pinard M., Lawton T., LaBoissiere S., Leathers V. L., Zou W. Q., Estey L. A., Lamontagne J., Lehto M. T., Kondejewski L. H., Francoeur G. P., Papadopoulos M., Haghighat A., Spatz S. J., Head M., Will R., Ironside J., O'Rourke K., Tonelli Q., Ledebur H. C., Chakrabartty A. and Cashman N. R. (2003) A prion protein epitope selective for the pathologically misfolded conformation. Nat. Med. 9, 893-9.

Peretz D., Williamson R. A., Kaneko K., Vergara J., Leclerc E., Schmitt-Ulms G., Mehihorn I. R., Legname G., Wormald M. R., Rudd P. M., Dwek R. A., Burton D. R. and Prusiner S. B. (2001) Antibodies inhibit prion propagation and clear cell cultures of prion infectivity. Nature 412, 739-743.

Pledger D. W., Brodnicki T. C., Graham B. L., Tetin S., Kranz D. M. and Linthicum D. S. (1999) Construction and characterization of two anti-sweetener single chain antibodies using radioligand binding, fluorescence and circular dichroism spectroscopy. J. Mol. Recognit. 12, 258-66.

Prusiner S. B. (1982) Novel proteinaceous infectious particles cause scrapie. Science 216, 136-144.

Prusiner S. B. (1998) Prions. Proc. Natl. Acad. Sci. USA 95, 13363-13383.

Prusiner S. B. (2001) Shattuck Lecture—Neurodegenerative diseases and prions. N. Engl. J. Med. 344, 1516-1526.

Safar J., Wille H., Itri V., Groth D., Serban H., Torchia M., Cohen F. E. and Prusiner S. B. (1998) Eight prion strains have $PrP^{Sc}$ molecules with different conformations. Nat. Med. 4, 1157-1165.

Safar J. G., Kellings K., Serban A., Groth D., Cleaver J. E., Prusiner S. B. and Riesner D. (2005) Search for a prion-specific nucleic acid. Journal of virology 79, 10796-806.

Schenk D., Barbour R., Dunn W., Gordon G., Grajeda H., Guido T., Hu K., Huang J., Johnson-Wood K., Khan K., Kholodenko D., Lee M., Liao Z., Lieberburg I., Motter R., Mutter L., Soriano F., Shopp G., Vasquez N., Vandevert C., Walker S., Wogulis M., Yednock T., Games D. and Seubert P. (1999) Immunization with amyloid-beta attenuates Alzheimer-disease-like pathology in the PDAPP mouse. Nature 400, 173-177.

Shirai H., Kidera A. and Nakamura H. (1996) Structural classification of CDR-H3 in antibodies. FEBS Lett 399, 1-8.

Solforosi et al. (2007) Journal of Biological Chemistry 282, 7465-71

Taylor J. P., Hardy J. and Fischbeck K. H. (2002) Toxic proteins in neurodegenerative disease. Science 296, 1991-5.

White A. R., Enever P., Tayebi M., Mushens R., Linehan J., Brandner S., Anstee D., Collinge J. and Hawke S. (2003) Monoclonal antibodies inhibit prion replication and delay the development of prion disease. Nature 422, 80-3.

The invention claimed is:

1. An isolated antibody or antibody fragment specifically recognizing a prion protein, comprising at least one amino acid sequence selected from a group consisting of
   a complementarity determining region (CDR) according to SEQ ID NO:1,
   a complementarity determining region (CDR) according to SEQ ID NO:11,
   a complementarity determining region (CDR) according to SEQ ID NO: 12, and
   a complementarity determining region (CDR) according to SEQ ID NO: 13.

2. The antibody or antibody fragment according to claim 1, wherein the complementarity determining region (CDR) is contained in at least one heavy chain variable region according to SEQ ID NO:4.

3. The antibody or antibody fragment according to claim 2, further comprising at least one light chain variable region according to SEQ ID NO:5.

4. The antibody or antibody fragment according to claim 3, wherein the at least one heavy chain variable region and the at least one light chain variable region are linked by a linker peptide.

5. The antibody or antibody fragment according to claim 1, further comprising at least one signal and/or tag sequence.

6. The antibody or antibody fragment according to claim 1, comprising the amino acid sequence according to SEQ ID NO:6.

7. A kit comprising the antibody or antibody fragment according to claim 1.

8. A pharmaceutical preparation comprising the antibody or antibody fragment according to claim 1.

9. The antibody or antibody fragment according to claim 4, wherein the linker peptide is $(Gly_4Ser)_3$.

* * * * *

SEQUENCE LISTING

<160> NUMBER OF SEQ ID NOS: 30

<210> SEQ ID NO 1
<211> LENGTH: 17
<212> TYPE: PRT
<213> ORGANISM: Mus musculus

<400> SEQUENCE: 1

Tyr Phe Cys Ala Arg Trp Asn Trp Glu Arg Asp Ala Met Asp Tyr Trp
1               5                   10                  15

Gly

<210> SEQ ID NO 2
<211> LENGTH: 17
<212> TYPE: PRT
<213> ORGANISM: Artificial
<220> FEATURE:
<223> OTHER INFORMATION: Retro-inverso D-peptide of CDR3H [(D-)riCDR3H]

<400> SEQUENCE: 2

Gly Trp Tyr Asp Met Ala Asp Arg Glu Trp Asn Trp Arg Ala Cys Phe
1               5                   10                  15

Tyr

<210> SEQ ID NO 3
<211> LENGTH: 268
<212> TYPE: PRT
<213> ORGANISM: Mus musculus

<400> SEQUENCE: 3

Met Ala Asp Val Lys Leu Gln Glu Ser Gly Ala Glu Leu Val Lys Pro
1               5                   10                  15

Gly Ala Ser Val Lys Leu Ser Cys Lys Ala Ser Gly Tyr Thr Phe Thr
                20                  25                  30

Ser Tyr Tyr Met Tyr Trp Val Lys Gln Arg Pro Gly Gln Gly Leu Glu
            35                  40                  45

Trp Ile Gly Glu Ile Asn Pro Ser Asn Gly Gly Thr Asn Phe Asn Glu
50                  55                  60

Lys Phe Lys Ser Lys Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Thr Arg Asp Tyr Arg Tyr Ala Trp Phe Ala Tyr Trp Gly Gln
            100                 105                 110

Gly Thr Leu Val Thr Val Ser Ala Glu Ser Gln Ser Phe Pro Asn Val
        115                 120                 125

Phe Pro Leu Ala Gly Gly Gly Ser Gly Gly Gly Ser Gly Gly
        130                 135                 140

Gly Gly Ser Asp Val Leu Met Thr Gln Thr Pro Leu Ser Leu Pro Val
145                 150                 155                 160

Ser Leu Gly Asp Gln Ala Ser Ile Ser Cys Arg Ser Gln Ser Ile
                165                 170                 175

Val His Ser Asn Gly Asn Thr Tyr Leu Glu Trp Tyr Leu Gln Lys Pro
            180                 185                 190

Gly Gln Ser Pro Lys Leu Leu Ile Tyr Lys Val Ser Asn Arg Phe Ser
        195                 200                 205

Gly Val Pro Asp Arg Phe Ser Gly Ser Gly Ser Gly Thr Asp Phe Thr
    210                 215                 220

```
Leu Lys Ile Ser Arg Val Glu Ala Glu Asp Leu Gly Val Tyr Tyr Cys
225                 230                 235                 240

Phe Gln Gly Ser His Val Pro Tyr Thr Phe Gly Gly Gly Thr Lys Leu
                245                 250                 255

Glu Ile Lys Arg Ala Asp Ala Ala Pro Thr Val Ser
            260                 265
```

<210> SEQ ID NO 4
<211> LENGTH: 179
<212> TYPE: PRT
<213> ORGANISM: Mus musculus

<400> SEQUENCE: 4

```
Met Lys Tyr Leu Leu Pro Thr Ala Ala Ala Gly Leu Leu Leu Leu Ala
1               5                   10                  15

Ala Gln Pro Ala Met Ala Met Ala Glu Val Gln Leu Gln Gln Ser Gly
                20                  25                  30

Ala Glu Leu Ala Arg Pro Gly Thr Ser Val Asn Leu Ser Cys Lys Thr
            35                  40                  45

Ser Gly Tyr Ser Phe Thr Gly Tyr Gly Val Ser Trp Val Lys Gln Arg
50                  55                  60

Ile Gly Gln Gly Leu Glu Trp Ile Gly Glu Ile Tyr Pro Arg Ser Gly
65                  70                  75                  80

Asn Thr Tyr Tyr Asn Glu Lys Phe Lys Gly Lys Ala Thr Leu Thr Ala
                85                  90                  95

Asp Lys Ser Ser Asn Thr Ala Tyr Met Glu Leu Arg Ser Leu Thr Ser
            100                 105                 110

Glu Asp Ser Ala Val Tyr Phe Cys Ala Arg Trp Asn Trp Glu Arg Asp
        115                 120                 125

Ala Met Asp Tyr Trp Gly Gln Gly Thr Ser Val Thr Val Ser Ser Ala
130                 135                 140

Lys Thr Thr Pro Pro Ser Asp Tyr Pro Leu Ala Gly Gly Gly Gly Ser
145                 150                 155                 160

Gly Gly Gly Gly Ser Gly Gly Gly Ser Asp Ile Val Met Thr Gln
                165                 170                 175

Thr Pro Leu
```

<210> SEQ ID NO 5
<211> LENGTH: 123
<212> TYPE: PRT
<213> ORGANISM: Mus musculus

<400> SEQUENCE: 5

```
Asp Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Ser Ser
                20                  25                  30

Ser Gly Tyr Pro His Leu Asn Trp Tyr Leu Gln Lys Pro Gly Gln Ser
            35                  40                  45

Pro Gln Leu Leu Ile Tyr Arg Val Ser Asn Arg Phe Ser Gly Val Leu
50                  55                  60

Asp Arg Phe Ser Gly Ser Gly Ser Gly Thr Asp Phe Thr Leu Gln Ile
65                  70                  75                  80

Ser Arg Val Glu Ala Glu Asp Leu Gly Val Tyr Phe Cys Leu Gln Ile
                85                  90                  95
```

Thr His Val Pro Trp Thr Phe Gly Gly Gly Thr Lys Leu Glu Ile Lys
            100                 105                 110

Arg Ala Asp Ala Ala Pro Thr Val Ser Ala Ala
        115                 120

<210> SEQ ID NO 6
<211> LENGTH: 311
<212> TYPE: PRT
<213> ORGANISM: Artificial
<220> FEATURE:
<223> OTHER INFORMATION: scFv

<400> SEQUENCE: 6

Met Lys Tyr Leu Leu Pro Thr Ala Ala Ala Gly Leu Leu Leu Leu Ala
1               5                   10                  15

Ala Gln Pro Ala Met Ala Met Ala Glu Val Gln Leu Gln Gln Ser Gly
            20                  25                  30

Ala Glu Leu Ala Arg Pro Gly Thr Ser Val Asn Leu Ser Cys Lys Thr
        35                  40                  45

Ser Gly Tyr Ser Phe Thr Gly Tyr Gly Val Ser Trp Val Lys Gln Arg
    50                  55                  60

Ile Gly Gln Gly Leu Glu Trp Ile Gly Glu Ile Tyr Pro Arg Ser Gly
65                  70                  75                  80

Asn Thr Tyr Tyr Asn Glu Lys Phe Lys Gly Lys Ala Thr Leu Thr Ala
                85                  90                  95

Asp Lys Ser Ser Asn Thr Ala Tyr Met Glu Leu Arg Ser Leu Thr Ser
            100                 105                 110

Glu Asp Ser Ala Val Tyr Phe Cys Ala Arg Trp Asn Trp Glu Arg Asp
        115                 120                 125

Ala Met Asp Tyr Trp Gly Gln Gly Thr Ser Val Thr Val Ser Ser Ala
    130                 135                 140

Lys Thr Thr Pro Pro Ser Asp Tyr Pro Leu Ala Gly Gly Gly Ser
145                 150                 155                 160

Gly Gly Gly Gly Ser Gly Gly Gly Ser Asp Ile Val Met Thr Gln
                165                 170                 175

Thr Pro Leu Ser Leu Pro Val Ser Leu Gly Asp Gln Ala Ser Ile Ser
            180                 185                 190

Cys Arg Ser Ser Gln Ser Leu Glu Ser Ser Ser Gly Tyr Pro His Leu
        195                 200                 205

Asn Trp Tyr Leu Gln Lys Pro Gly Gln Ser Pro Gln Leu Leu Ile Tyr
    210                 215                 220

Arg Val Ser Asn Arg Phe Ser Gly Val Leu Asp Arg Phe Ser Gly Ser
225                 230                 235                 240

Gly Ser Gly Thr Asp Phe Thr Leu Gln Ile Ser Arg Val Glu Ala Glu
                245                 250                 255

Asp Leu Gly Val Tyr Phe Cys Leu Gln Ile Thr His Val Pro Trp Thr
            260                 265                 270

Phe Gly Gly Gly Thr Lys Leu Glu Ile Lys Arg Ala Asp Ala Ala Pro
        275                 280                 285

Thr Val Ser Ala Ala Glu Gln Lys Leu Ile Ser Glu Glu Asp Leu
    290                 295                 300

Glu His His His His His His
305                 310

<210> SEQ ID NO 7
<211> LENGTH: 821

```
<212> TYPE: DNA
<213> ORGANISM: Mus musculus

<400> SEQUENCE: 7
aaaaccatgg cggatgtgaa gcttcaggag tctggggctg aactggtgaa gcctggggct        60
tcagtgaagt tgtcctgcaa ggcttctggc tacaccttca ccagctacta tatgtactgg       120
gtgaagcaga ggcctggaca aggccttgag tggattggag agattaatcc tagcaatggt       180
ggtactaact tcaatgagaa gttcaagagc aaggccacac tgactgtaga caaatcctcc       240
agcacagcat acatgcaact cagcagcctg acatctgagg actctgcggt ctattactgt       300
acaagagact ataggtacgc ctggtttgct tactggggcc aagggactct ggtcactgtc       360
tctgcagaga gtcagtcctt cccaaatgtc ttccccctcg ccggcggagg cggttcaggc       420
ggaggtggct ctggcggtgg cggatccgat gttttgatga cccaaactcc actctccctg       480
cctgtcagtc ttggagatca agcctccatc tcttgcagat ctagtcagag cattgtacat       540
agtaatggaa acacctattt agaatggtac ctgcagaaac caggccagtc tccaaagctc       600
ctgatctaca agtttccaac cgatttcct ggggtcccag acaggttcag tggcagtgga       660
tcagggacag atttcacact caagatcagc agagtggagg ctgaggatct gggagtttat       720
tactgctttc aaggttcaca tgttccgtac acgttcggag ggggaccaa gctggaaata       780 aaacgggctg atgctgcacc aactgtatcc ggccgctttt                             821

<210> SEQ ID NO 8
<211> LENGTH: 480
<212> TYPE: DNA
<213> ORGANISM: Mus musculus

<400> SEQUENCE: 8
atgaaatacc tgctgccgac cgctgctgct ggtctgctgc tcctcgctgc ccagccggcg        60
atggccatgg cggaggtcca gctgcagcag tctggagctg agctggcgag gcctgggact       120
tcagtgaacc tgtcttgtaa gacttctggc tacagcttca caggctatgg tgtaagttgg       180
gtgaagcagc gaattggaca gggccttgag tggattggag agatttatcc tagaagtggt       240
aatacttact acaatgagaa gttcaagggc aaggccacac tgactgcaga caaatcctcc       300
aacacggcgt acatggagct ccgcagcctg acatctgagg actctgcggt ctatttctgt       360
gcaagatgga actgggaaag ggatgcaatg gactactggg gtcaaggaac ctcagtcacc       420
gtctcctcag ccaaaacgac accccatct gactatccac tagccggcgg aggcggttca       480

<210> SEQ ID NO 9
<211> LENGTH: 369
<212> TYPE: DNA
<213> ORGANISM: Mus musculus

<400> SEQUENCE: 9
gacattgtga tgacccaaac tccactctcc ctgcctgtca gtcttggaga tcaagcctcc        60
atctcttgca ggtctagtca gagccttgaa agcagtagtg gatatcccca tttgaactgg       120
tacctccaga aaccaggcca gtctccacaa ctcctgatct acaggtttc caaccgattt       180 tctggggtcc tagacaggtt cagtggtagt ggatcaggga cagatttcac actgcaaatc       240
agcagagtgg aggctgagga tttgggagtt tatttctgcc tccaaattac acatgtcccg       300
tggacgttcg gtgaggcac caagctggaa atcaaacggg ctgatgctgc accaactgta       360
tccgcggcc                                                               369
```

-continued

```
<210> SEQ ID NO 10
<211> LENGTH: 936
<212> TYPE: DNA
<213> ORGANISM: Artificial
<220> FEATURE:
<223> OTHER INFORMATION: scFv Myc-His (H6/L5)

<400> SEQUENCE: 10
atgaaatacc tgctgccgac cgctgctgct ggtctgctgc tcctcgctgc ccagccggcg     60
atggccatgg cggaggtcca gctgcagcag tctggagctg agctggcgag gcctgggact    120
tcagtgaacc tgtcttgtaa gacttctggc tacagcttca caggctatgg tgtaagttgg    180
gtgaagcagc gaattggaca gggccttgag tggattggag agatttatcc tagaagtggt    240
aatacttact acaatgagaa gttcaagggc aaggccacac tgactgcaga caaatcctcc    300
aacacggcgt acatggagct ccgcagcctg acatctgagg actctgcggt ctatttctgt    360
gcaagatgga ctgggaaag ggatgcaatg gactactggg gtcaaggaac ctcagtcacc     420
gtctcctcag ccaaaacgac acccccatct gactatccac tagccggcgg aggcggttca    480
ggcggaggtg gctctggcgg tggcggatcc gacattgtga tgacccaaac tccactctcc    540
ctgcctgtca gtcttggaga tcaagcctcc atctcttgca ggtctagtca gagccttgaa    600
agcagtagtg gatatcccca tttgaactgg tacctccaga aaccaggcca gtctccacaa    660
ctcctgatct acagggtttc caaccgattt tctggggtcc tagacaggtt cagtggtagt    720
ggatcaggga cagatttcac actgcaaatc agcagagtgg aggctgagga tttgggagtt    780
tatttctgcc tccaaattac acatgtcccg tggacgttcg gtggaggcac caagctggaa    840
atcaaacggg ctgatgctgc accaactgta tccgcggccg aagaacagaa actgatcagc    900
gaagaagatc tcgagcacca ccaccaccac cactga                              936

<210> SEQ ID NO 11
<211> LENGTH: 17
<212> TYPE: PRT
<213> ORGANISM: Artificial
<220> FEATURE:
<223> OTHER INFORMATION: M13A mutant of CDR3H

<400> SEQUENCE: 11

Tyr Phe Cys Ala Arg Trp Asn Trp Glu Arg Asp Ala Ala Asp Tyr Trp
1               5                   10                  15

Gly

<210> SEQ ID NO 12
<211> LENGTH: 17
<212> TYPE: PRT
<213> ORGANISM: Artificial
<220> FEATURE:
<223> OTHER INFORMATION: D11R mutant of CDR3H

<400> SEQUENCE: 12

Tyr Phe Cys Ala Arg Trp Asn Trp Glu Arg Arg Ala Met Asp Tyr Trp
1               5                   10                  15

Gly

<210> SEQ ID NO 13
<211> LENGTH: 17
<212> TYPE: PRT
<213> ORGANISM: Artificial
<220> FEATURE:
<223> OTHER INFORMATION: R10A mutant of CDR3H
```

```
<400> SEQUENCE: 13

Tyr Phe Cys Ala Arg Trp Asn Trp Glu Ala Asp Ala Met Asp Tyr Trp
1               5                   10                  15

Gly

<210> SEQ ID NO 14
<211> LENGTH: 17
<212> TYPE: PRT
<213> ORGANISM: Artificial
<220> FEATURE:
<223> OTHER INFORMATION: C3A mutant of CDR3H

<400> SEQUENCE: 14

Tyr Phe Ala Ala Arg Trp Asn Trp Glu Arg Asp Ala Met Asp Tyr Trp
1               5                   10                  15

Gly

<210> SEQ ID NO 15
<211> LENGTH: 17
<212> TYPE: PRT
<213> ORGANISM: Artificial
<220> FEATURE:
<223> OTHER INFORMATION: R5A mutant of CDR3H

<400> SEQUENCE: 15

Tyr Phe Cys Ala Ala Trp Asn Trp Glu Arg Asp Ala Met Asp Tyr Trp
1               5                   10                  15

Gly

<210> SEQ ID NO 16
<211> LENGTH: 17
<212> TYPE: PRT
<213> ORGANISM: Artificial
<220> FEATURE:
<223> OTHER INFORMATION: W6A mutant of CDR3H

<400> SEQUENCE: 16

Tyr Phe Cys Ala Arg Ala Asn Trp Glu Arg Asp Ala Met Asp Tyr Trp
1               5                   10                  15

Gly

<210> SEQ ID NO 17
<211> LENGTH: 17
<212> TYPE: PRT
<213> ORGANISM: Artificial
<220> FEATURE:
<223> OTHER INFORMATION: N7A mutant of CDR3H

<400> SEQUENCE: 17

Tyr Phe Cys Ala Arg Trp Ala Trp Glu Arg Asp Ala Met Asp Tyr Trp
1               5                   10                  15

Gly

<210> SEQ ID NO 18
<211> LENGTH: 17
<212> TYPE: PRT
<213> ORGANISM: Artificial
<220> FEATURE:
<223> OTHER INFORMATION: W8A mutant of CDR3H

<400> SEQUENCE: 18

Tyr Phe Cys Ala Arg Trp Asn Ala Glu Arg Asp Ala Met Asp Tyr Trp
```

Gly

```
<210> SEQ ID NO 19
<211> LENGTH: 17
<212> TYPE: PRT
<213> ORGANISM: Artificial
<220> FEATURE:
<223> OTHER INFORMATION: E9A mutant of CDR3H

<400> SEQUENCE: 19
```

Tyr Phe Cys Ala Arg Trp Asn Trp Ala Arg Asp Ala Met Asp Tyr Trp
1               5                   10                  15

Gly

```
<210> SEQ ID NO 20
<211> LENGTH: 17
<212> TYPE: PRT
<213> ORGANISM: Artificial
<220> FEATURE:
<223> OTHER INFORMATION: D11A mutant of CDR3H

<400> SEQUENCE: 20
```

Tyr Phe Cys Ala Arg Trp Asn Trp Glu Arg Ala Ala Met Asp Tyr Trp
1               5                   10                  15

Gly

```
<210> SEQ ID NO 21
<211> LENGTH: 17
<212> TYPE: PRT
<213> ORGANISM: Artificial
<220> FEATURE:
<223> OTHER INFORMATION: D14A mutant of CDR3H

<400> SEQUENCE: 21
```

Tyr Phe Cys Ala Arg Trp Asn Trp Glu Arg Asp Ala Met Ala Tyr Trp
1               5                   10                  15

Gly

```
<210> SEQ ID NO 22
<211> LENGTH: 17
<212> TYPE: PRT
<213> ORGANISM: Artificial
<220> FEATURE:
<223> OTHER INFORMATION: Y15A mutant of CDR3H

<400> SEQUENCE: 22
```

Tyr Phe Cys Ala Arg Trp Asn Trp Glu Arg Asp Ala Met Asp Ala Trp
1               5                   10                  15

Gly

```
<210> SEQ ID NO 23
<211> LENGTH: 17
<212> TYPE: PRT
<213> ORGANISM: Artificial
<220> FEATURE:
<223> OTHER INFORMATION: R5D mutant of CDR3H

<400> SEQUENCE: 23
```

Tyr Phe Cys Ala Asp Trp Asn Trp Glu Arg Asp Ala Met Asp Tyr Trp
1               5                   10                  15

Gly

<210> SEQ ID NO 24
<211> LENGTH: 17
<212> TYPE: PRT
<213> ORGANISM: Artificial
<220> FEATURE:
<223> OTHER INFORMATION: E9R mutant of CDR3H

<400> SEQUENCE: 24

Tyr Phe Cys Ala Arg Trp Asn Trp Arg Arg Asp Ala Met Asp Tyr Trp
1               5                   10                  15

Gly

<210> SEQ ID NO 25
<211> LENGTH: 17
<212> TYPE: PRT
<213> ORGANISM: Artificial
<220> FEATURE:
<223> OTHER INFORMATION: R10D mutant of CDR3H

<400> SEQUENCE: 25

Tyr Phe Cys Ala Arg Trp Asn Trp Glu Asp Asp Ala Met Asp Tyr Trp
1               5                   10                  15

Gly

<210> SEQ ID NO 26
<211> LENGTH: 17
<212> TYPE: PRT
<213> ORGANISM: Artificial
<220> FEATURE:
<223> OTHER INFORMATION: D14R mutant of CDR3H

<400> SEQUENCE: 26

Tyr Phe Cys Ala Arg Trp Asn Trp Glu Arg Asp Ala Met Arg Tyr Trp
1               5                   10                  15

Gly

<210> SEQ ID NO 27
<211> LENGTH: 32
<212> TYPE: DNA
<213> ORGANISM: Artificial
<220> FEATURE:
<223> OTHER INFORMATION: primer

<400> SEQUENCE: 27
aaaaccatgg cggaggtcca gctgcagcag tc                                    32

<210> SEQ ID NO 28
<211> LENGTH: 43
<212> TYPE: DNA
<213> ORGANISM: Artificial
<220> FEATURE:
<223> OTHER INFORMATION: primer

<400> SEQUENCE: 28
ttttgccggc cagtggatag tcagatgggg gtgtcgtttt ggc                        43

<210> SEQ ID NO 29
<211> LENGTH: 30
<212> TYPE: DNA
<213> ORGANISM: Artificial
<220> FEATURE:
<223> OTHER INFORMATION: primer

<400> SEQUENCE: 29

| | |
|---|---|
| aaaggatccg acattgtgat gacccagtct | 30 |

<210> SEQ ID NO 30
<211> LENGTH: 33
<212> TYPE: DNA
<213> ORGANISM: Artificial
<220> FEATURE:
<223> OTHER INFORMATION: primer

<400> SEQUENCE: 30

| | |
|---|---|
| aaaagcggcc gcggatacag ttggtgcagc atc | 33 |